(12) United States Patent
Dzerins et al.

(10) Patent No.: US 11,690,673 B2
(45) Date of Patent: Jul. 4, 2023

(54) DEVICE FOR TREATMENT OF BODY TISSUE

(71) Applicant: SIA LIGHT GUIDE OPTICS INTERNATIONAL, Livani (LV)

(72) Inventors: Oskars Dzerins, Madona (LV); Daumants Pfafrods, Livani (LV)

(73) Assignee: SIA LIGHT GUIDE OPTICS INTERNATIONAL, Livani (LV)

( * ) Notice: Subject to any disclaimer, the term of this patent is extended or adjusted under 35 U.S.C. 154(b) by 342 days.

(21) Appl. No.: 16/976,539

(22) PCT Filed: Sep. 19, 2019

(86) PCT No.: PCT/EP2019/075244
§ 371 (c)(1),
(2) Date: Aug. 28, 2020

(87) PCT Pub. No.: WO2020/058447
PCT Pub. Date: Mar. 26, 2020

(65) Prior Publication Data
US 2020/0405390 A1 Dec. 31, 2020

(30) Foreign Application Priority Data
Sep. 20, 2018 (EP) .................................... 18000750

(51) Int. Cl.
*A61B 18/24* (2006.01)
*A61N 5/06* (2006.01)
(Continued)

(52) U.S. Cl.
CPC .............. *A61B 18/24* (2013.01); *A61L 29/02* (2013.01); *A61L 29/106* (2013.01); *A61N 5/062* (2013.01);
(Continued)

(58) Field of Classification Search
CPC .............. A61B 18/24; A61B 17/12031; A61B 2018/00404; A61B 2018/2261;
(Continued)

(56) References Cited

U.S. PATENT DOCUMENTS 9,693,826 B2 * 7/2017 Neuberger ............. A61B 18/24
11,399,892 B2 * 8/2022 Yu .......................... A61B 18/22
(Continued)

FOREIGN PATENT DOCUMENTS

EP 0598984 A1 6/1994
FR 1325014 A 4/1963

OTHER PUBLICATIONS

"The Physics Behind Fiber Optics, Apr. 23, 2004, Cisco Press, https://www.ciscopress.com/articles/article.asp?p=170740&seqNum=3" (Year: 2004).*
(Continued)

*Primary Examiner* — Joseph M Dietrich
*Assistant Examiner* — Michael T. Holtzclaw
(74) *Attorney, Agent, or Firm* — Jason H. Vick; Sheridan Ross, PC

(57) ABSTRACT

The invention relates to a device (17) for treatment of body tissue, in particular for the permanent occlusion of varicose veins, preferably in the lower limbs, of varicocele and/or of vascular malformations and/or for the use in aesthetic surgeries, preferably laser assisted lipolysis, and/or for tumor treatment by means of laser induced thermotherapy and/or photodynamic therapy, by means of a light diffuser (13) circumferentially and endoluminally irradiating said tissue by laser light energy, said diffuser (13) being connected at its proximal end to a source (10) of laser light energy via a flexible wave guide (12) comprising a fiber optic core (1) covered by an optical cladding (2) having a refractive index smaller than that of the core (1), wherein in the cladding (2)

(Continued)

and/or in the core (1) imperfections (18) are provided, designed as recesses and adapted to direct the light, preferably to refract and/or reflect the light propagating within the core (1) and/or its optical cladding (2) in generally radial directions, wherein a cap (7) transparent to the laser light enclosing the distal end of the core (1) and its optical cladding (2) in a fluid tight and/or liquid tight manner is provided. According to the invention the device (17) is characterized in that the outer surface (19) of said optical cladding (2) is fused in the region (A) between said imperfections (18) to the inner surface (21), preferably the inner diameter, of the cap (7) and/or in that the outer surface (19) of said optical cladding (2) extending over a distance in front and/or behind the region (A) provided with the imperfections (18) is fused to the inner surface (21), preferably the inner diameter, of the cap (7).

28 Claims, 7 Drawing Sheets

(51) Int. Cl.

| | | |
|---|---|---|
| *A61B 17/12* | (2006.01) | |
| *A61B 18/00* | (2006.01) | |
| *A61B 18/22* | (2006.01) | |
| *A61N 5/067* | (2006.01) | |
| *A61L 29/02* | (2006.01) | |
| *A61L 29/10* | (2006.01) | |

(52) U.S. Cl.
CPC ...... *A61N 5/0625* (2013.01); *A61B 17/12031* (2013.01); *A61B 2018/00404* (2013.01); *A61B 2018/2261* (2013.01); *A61N 5/067* (2021.08); *A61N 2005/0602* (2013.01); *A61N 2005/0631* (2013.01)

(58) Field of Classification Search
CPC . A61B 2018/2277; A61B 18/22; A61L 29/02; A61L 29/106; A61N 5/062; A61N 5/0625; A61N 5/067; A61N 2005/0602; A61N 2005/0631
See application file for complete search history.

(56) References Cited

U.S. PATENT DOCUMENTS

| | | | |
|---|---|---|---|
| 2007/0179488 A1 | 8/2007 | Trusty et al. | |
| 2009/0248004 A1* | 10/2009 | Altshuler | A61B 18/203 |
| | | | 606/33 |
| 2010/0179525 A1 | 7/2010 | Neuberger | |
| 2010/0262131 A1* | 10/2010 | Neuberger | A61B 18/22 |
| | | | 606/16 |
| 2011/0282330 A1* | 11/2011 | Harschack | A61B 18/24 |
| | | | 606/15 |
| 2015/0057648 A1 | 2/2015 | Swift et al. | |
| 2017/0119469 A1 | 5/2017 | Shimizu et al. | |
| 2017/0135765 A1* | 5/2017 | Griffin | G02B 6/0003 |
| 2020/0222712 A1* | 7/2020 | Schultheis | G02B 5/0242 |

OTHER PUBLICATIONS

"Quartz vs. Fused Silica: What's the Difference?, Sep. 8, 2015, Swift Glass, https://www.swiftglass.com/blog/quartz-vs-fused-silica-whats-the-difference/" (Year: 2015).*
"Boyd, et al., CO2 laser-fabricated cladding light strippers for high-power fiber lasers and amplifiers, Apr. 10, 2016, Applied Optics, vol. 55, No. 11" (Year: 2016).*
International Search Report for International Application No. PCT/EP2019/075244, dated Dec. 17, 2019.
Written Opinion for International Application No. PCT/EP2019/075244, dated Dec. 17, 2019.

* cited by examiner

2

DEVICE FOR TREATMENT OF BODY TISSUE

CROSS-REFERENCE TO RELATED APPLICATIONS

This application is a national stage application under 35 U.S.C. 371 of PCT Application No. PCT/EP2019/075244 having an international filing date of 19 Sep. 2019, which designated the United States, which PCT application claimed the benefit of European Application No. 18000750.2, filed 20 Sep. 2018, each of which are incorporated herein by reference in their entirety.

This invention relates to a device for treatment of body tissue by means of a laser light diffuser circumferentially and endoluminally irradiating said tissue by laser light.

In particular, the device for treatment of body tissue is intended for the use for the permanent occlusion of varicose veins, preferably in the lower limbs. Moreover, the device is preferably intended for the use for the permanent occlusion of varicocele and/or vascular malformations. Alternatively or additionally, the device can be intended for the use in aesthetic surgeries, in particular such as laser assisted lipolysis, and/or for tumor treatment, preferably by means of laser induced thermotherapy (LITT) and/or photodynamic therapy (PDT).

Said diffuser is connected at its proximal end to a source of laser light energy via a flexible wave guide comprising a fiber optic core covered by an optical cladding having a refractive index smaller than that of the core. Imperfections are provided in the cladding and/or in the core, wherein the imperfections are adapted to direct the light, preferably to refract and/or reflect the light propagating within the core and/or its optical cladding in generally radial directions. The imperfections are designed as recesses.

The imperfections designed as recesses can extend at least into the cladding and, preferably, into the core. In particular, the imperfections designed as recesses can differ from one another, in particular with regard to the depth. Preferably, at least one imperfection can extend solely into the cladding—and therefore not into the core—, wherein at least one further imperfection can extend into the cladding as well as into the core.

Furthermore, a cap is provided, wherein the cap is transparent to the laser light, enclosing the distal end of the core and its optical cladding in a fluid tight and/or liquid tight manner. The laser light can pass through the optical cladding and the cap.

In the medical field, diffusers are generally used on the distal end of the wave guide as a means for scattering and/or redirecting the optical power in an even 360-degree cylindrical output along the length of the distal end of the core of the wave guide. This is for instance facilitated by roughening the core or by machining imperfections designed as grooves or threads into the glass of the fiber core deep enough to extract and scatter and/or redirect light travelling through the fiber core along the longitudinal axis thereof. The light emerging from the imperfections or grooves irradiates an area of the tissue surrounding the diffuser with the optical power, making it useful for applications such as photodynamic therapy or coagulation and/or ablation of tissue, vessels or hollow organs. To protect the distal end of the core which has its protective sheath removed, this distal end is conventionally surrounded and covered by a cap transparent to the laser light emitted by the core.

In the field of illumination, it is known since long time to direct light from point light sources into one or both ends of a cylindrical rod made of refractive material and to redirect the light propagating within the rod in radial and circumferential directions of the rod by cutting either circular or spiral grooves into the outer surface of the rod as shown in FR 1 325 014. The light travelling within the rod exits therefrom at said grooves. If light is directed into the rod from only one end thereof, it is possible to terminate the other end by a conical reflector. In order to obtain a uniform radiation distribution over the length of the rod, it is further known to use deeper groves at positions of the rod more distant from the light sources to improve the uniform radiation distribution.

The same principle also is used in the medical field as exemplified in an embodiment of a laser light diffuser shown in FIG. 6 of EP 0 598 984 A1. In this embodiment, angled grooves are cut into the core of a wave guide under an angle to the longitudinal axis thereof. Further, this embodiment is provided with a conical reflector at the distal end of the core, and the section of the core comprising the groove as well as the conical reflector is enclosed in a cap transparent to the laser light.

The design of such diffusers varies depending on the desired length of the light emitting zone and light uniformity required as well as the available laser light energy.

In practice, it has been found that in a few cases after the treatment of the body tissue, the cap remains in the body tissue of the patient, wherein the core and the wave guide have been pulled out of the body tissue. Unfortunately, the remaining of the cap in the body tissue is a risk for infections and therefore endangers the health of the patient. Not only the risk of an infection increases due to use of the known diffusers, but also the seceded cap and/or the aborted cap may rupture the body tissue and hence can lead to an internal bleeding.

The risk, that the light diffuser together with the core is pulled out of the body tissue, while solely the cap remains in the body tissue, cannot be prevented in the known devices.

The object of the present invention is to provide a device for treatment of body tissue by means of a laser light diffuser which avoids or at least reduces the disadvantages of the prior art.

The present invention relates to a device for treatment of body tissue, in particular for the permanent occlusion of varicose veins, preferably in the lower limbs, of varicocele and/or of vascular malformations and/or for the use in aesthetic surgeries, preferably laser assisted lipolysis, and/or for tumor treatments, by means of laser induced thermotherapy and/or photodynamic therapy, by means of a light diffuser circumferentially and endoluminally irradiating said tissue by laser light energy, said diffuser being connected at its proximal end to a source of laser light energy via a flexible wave guide comprising a fiber optic core covered by an optical cladding having a refractive index smaller than that of the core, wherein in the cladding and/or in the core as recesses designed imperfections adapted to direct the light, preferably to refract and/or reflect the light propagating within the core and/or its optical cladding in generally radial directions, are provided, and wherein a cap transparent to the laser light enclosing the distal end of the core and its optical cladding in a fluid tight and/or liquid tight manner is provided.

The fiber core is coaxially surrounded by the cladding, in particular wherein a jacket mechanically protects the core, and prevents, in particular, the fiber from breaking during the use or transport.

The cladding is in particular intended to prevent the light waves from escaping or being emitted out of the core. Light energy travels in the path of the least resistance. As light waves in particular travel down the core and encounter the etching of the core and imperfections of the cladding and/or core the waves will begin to escape through the imperfections and be emitted into the surrounding vessel and/or vein.

The inventive device for treatment of body tissue is characterized in that the outer surface of said optical cladding is fused in the region between said imperfections to the inner surface, in particular the inner diameter, of the cap. Alternatively or additionally, the inventive device for treatment of body tissue is characterized in that the outer surface of said optical cladding extending over a distance in front and/or behind the region provided with the imperfections is fused to the inner surface, in particular the inner diameter, of the cap.

According to the invention the cap is fused at least partially and/or at least in partial areas, namely at least to the optical cladding in the region between the imperfections and/or—at least partially—in the regions in front (before) and/or behind the imperfections.

The region in front and/or behind the region provided with the imperfections refers in particular to the direction of the laser light propagation, in particular wherein the laser light first travels through the region in front of the region provided with the imperfections, then through the region provided with the imperfections and subsequently through the region behind the region provided with the imperfections.

Due to the fusing of the cap and the optical cladding the cap is, in particular, firmly bonded to the optical cladding and cannot be pulled off during the treatment of the body tissue. The invention preferably enables to overcome the disadvantages of the prior art with regard to the detachment and/or removal of the cap during the treatment of the body tissue. The cap can be firmly attached to the optical cladding at least in the fused region and/or in the fused partial areas. The invention reduces the risk for infections on the basis of the treatment of the body tissue with the device. In particular, an unexpected and/or an unintended detachment and/or removal of the cap, e.g. in the veins of the patient, is avoided.

Furthermore, the fluid tight and/or liquid tight enclosing of the distal end of the core is improved for the reason that the cap is not only bonded at its distal end to the wave guide.

Preferably, a short longitudinal length of the bared optical cladding of the core preceding and/or following the region provided with the imperfections can be fused to the cladding of the cap, in particular to counter the reduced mechanical stability caused by the imperfections. The inner diameter of the cap is preferably about the same as the outer diameter of the core—inclusive its optical cladding. The optical cladding can be fused at least in some regions and/or partial areas between said imperfections to the inner diameter of the cap as well.

Further, the device can be used for the medical application field "phlebology".

The source of laser light may be a conventional laser source or a diode laser source.

Whether the light is refracted or reflected depends in particular on the form of the imperfections and the angle of incidence of the laser light. The angle of incidence can be of such a size that a total internal reflection occurs. Moreover, a refraction or reflection of the light can depend on the relation of the refractive indices. For light, refraction follows in particular Snell's law which states that for a given pair of media the ratio of the sines of the angle of incidence $\alpha_1$ and the angle of refraction $\alpha 2$ is equal to the ratio of the indices of refraction $(n_2/n_1)$ of the two media. The index 1 refers to the first media, namely the core, wherein the index 2 refers to the second media, namely the cladding:

$$\frac{\sin\alpha_1}{\sin\alpha_2} = \frac{n_2}{n_1}$$

The total internal reflection is in particular defined by the critical angle. If the angle of incidence is greater than the critical angle, total internal reflection occurs. The light is reflected. Assuming that light waves or other electromagnetic waves are propagating in an isotropic media, there is a well-known formula for the critical angle in terms of the refractive indices. The angle of incidence has to be grater than $$\alpha_{crit} = \arcsin\left(\frac{n_2}{n_1}\right),$$

for total internal reflection, wherein the index crit is referring to the critical angle.

According to a preferred embodiment of the invention, the outer surface of said optical cladding is fused continuously and/or circumferentially and/or fully in the region between said imperfections to the inner surface, in particular the inner diameter, of the cap. Therefore, the fused region between said imperfections is designed in such a way that the fused region, in particular the fused partial area, is provided continuously and/or circumferentially and/or fully. This can in particular ensure the firm attachment of the cap to the optical cladding.

Alternatively or additionally, the outer surface of said optical cladding extending over a distance in front and/or behind the region provided with the imperfections is fused, preferably continuously and/or circumferentially and/or fully, to the inner surface, in particular the inner diameter, of the cap. Therefore, the fused region—in particular the region between said imperfections—and/or the region in front and/or behind the region provided with the imperfections can be fused in such a way that the fused area can be provided 360 degrees circumferential around the optical cladding.

In another preferred embodiment the outer surface of said optical cladding is fused partially, preferably in a point-like manner and/or with longitudinal welds, in the region between said imperfections to the inner surface, in particular the inner diameter, of the cap and/or the outer surface of said optical cladding extending over a distance in front and/or behind the region provided with the imperfections is fused partially, preferably in a point-like manner and/or with longitudinal welds, to the inner surface, in particular the inner diameter, of the cap. Therefore, the fused area can be provided in several fused regions (fused partial areas), in particular wherein the fused regions are designed as partial sections. It has been found in experiments that have been carried out in connection with the invention that even partially fused region(s) can provide a firm attachment of the cap to the optical cladding. The design of the fused region(s) depends in particular on the fusing method of the optical cladding to the cap.

Moreover, there can be non-fused regions between the optical cladding and the cap in which there are no imperfections provided and/or in which the cap is not fused to the cladding. The fused area between the cap and the optical cladding can be provided via the fused regions (partial areas) which can—in each case—be designed as a full and/or partial surface applied fusing. The fused partial areas enable in particular the firm attachment of the cap to the optical cladding, wherein according to the invention the design of the fused area and/or the fused region(s) can depend on the fusing method.

Furthermore, in the fused regions, in which the cladding is fused to the cap (fused regions), the cladding and the cap are, preferably, firmly bonded, in particular in a material-locking manner. In particular, no additional glue is necessary for the firmly bonding of the cap and the cladding in the fused regions. Due to the material-locking manner of the bonding of the cladding and the cap, the cap is inseparable and/or inextricably linked and/or connected to the cladding. Preferably, the cap cannot be detached from the cladding.

More preferably, the core has an inner diameter between 100 and 1000 μm, preferably between 200 and 800 μm, more preferably between 300 and 700 μm and in particular between 350 and 600 μm. These diameter ranges enable in particular to direct the light and further to provide the imperfections which can extend into the core. The imperfections can surround the core circumferentially so that the diameter has to be great enough with regard to the needed depth of the imperfections.

The outer diameter of the cladding can be greater as the outer diameter of the core for the reason that the cladding surrounds—at least partially—the core. The cladding can have an outer diameter between 110 and 1200 μm, preferably between 250 and 850 μm, more preferably between 350 and 750 μm and in particular between 400 and 650 μm.

In particular, the core can have a diameter between 530 and 555 μm, in particular wherein the cladding can have an outer diameter between 580 and 610 μm.

Alternatively or additionally, the core can have an outer diameter between 380 and 410 μm, in particular wherein the cladding can have an outer diameter between 420 and 450 μm.

Further, the sheath thickness of the cladding can be between 1% to 40%, preferably between 5% to 20%, of the outer diameter of the core. Therefore, the thickness of the cladding can depend on the outer diameter of the core.

In addition, a protective sheath can be provided, preferably at the distal end of the wave guide. The protective sheath can be joined to the cap. The protective sheath can further surround the optical cladding and/or the core. Preferably, the protective sheath is designed in such a way that the light directed through the core cannot be transmitted via/over the protective sheath. In particular, the protective sheath can comprise at least one buffer layer, preferably adjacent to the optical cladding of the core, and/or an outer sheath. The outer sheath can be designed as a jacket which surrounds at least the core.

The buffer layer can further be placed adjacent to the cap and/or between the cap and the core, preferably in a non-fused region. Alternatively or additionally, the buffer layer can be adjacent and/or adjoin on the outer sheath and/or the outer sheath can be adjacent and/or adjoin on the cap, preferably at least indirectly.

The protective sheath and/or the outer sheath can further be designed as a, preferably extruded, plastic coating.

In addition, the outer sheath can be joined to the cap.

According to another preferred embodiment of the present invention, the device can be characterized in that the protective sheath and/or the outer sheath (also called jacket) is at least partially removed at the distal end of the wave guide to bare the core and its optical cladding. Therefore, the distal end of the wave guide can be designed with the protective sheath being removed, in particular so that the core and its optical cladding can face the cap.

Preferably, the imperfections can extend into the cladding, preferably to bare the core, and/or into the core. The depth and/or the width—in particular the extension into the cladding and/or into the core—can be designed in such a way—depending of the form of the imperfections—that the light transmitted and directed along the core can be decoupled or coupled out and therefore can be sent out or emitted via the optical cladding and the cap. The light is reflected and/or refracted by the imperfections, wherein the form of the imperfections can be designed in such a way that the greater percentage of the light can either be refracted or reflected. The imperfections can reduce the sheath thickness of the cladding within the imperfections and therefore can change the light propagation behavior.

Further, the imperfections can be designed as grooves, in particular spiral grooves, that are adapted to refract and/or reflect the light propagating within the core and its optical cladding in generally radial directions.

The grooves can comprise at least two spiral grooves that extend through the optical cladding into the core. Alternatively or additionally, the grooves can extend at least into the cladding and, preferably, into the core. The depth and/or the width of the grooves can vary, in particular wherein the depth and/or width of the grooves can increase in the direction of the distal end of the core.

The successive grooves of the respective spiral grooves can alternate along the outer surface longitudinally extending from the core and its optical cladding.

In another preferred embodiment of the present invention, the imperfections can comprise at least one circular and/or elliptical groove and/or ring-like groove. The circular groove can surround the core and the cladding circumferentially.

Moreover, the imperfections can also comprise at least one longitudinal groove. Also a point-like and/or broken imperfection/groove and/or a recess in the form of a spherical cap is possible. The form of the imperfections/grooves can vary. Also a combination of different forms of imperfections/grooves is possible.

The imperfections/grooves are designed in such a way that the light propagating within the core can be emitted out or coupled out of the core and the cladding. The light is reflected and/or refracted on the boundary surface of the imperfection/groove. The greater the depth and/or width of the imperfections/grooves is, the greater the percentage of the intensity of the light will be which "leaves" (is emitted) the core and the cladding—for the reason that the light is in particular refracted on the boundary surface of the imperfections/grooves.

The imperfections can also be provided in a patterned structure and/or with different forms. In particular, the pattern of the imperfections is designed in such a way that a substantially uniform emission profile is reached over the length of the region provided with the imperfections.

In a further preferred embodiment of the present invention, the depth and/or the width and/or the length of the imperfections, preferably of the grooves, increases in a direction of the distal end of the core. In particular, the depth and/or the width and/or the length, preferably the depth and the width, of the imperfections increases up to 1000%, preferably up to 800%, more preferably up to 400%, in particular with regard to the smallest depth and/or width and/or length of the imperfections.

Preferably, the greatest depth and/or width of the imperfections is between two to four times greater than the depth and/or width of the smallest depth and/or width of the imperfections.

In particular, the depth and or width of the imperfection can increase up to 400 µm, preferably up to 300 µm, more preferably up to 200 µm and/or the depth and or width of the imperfections can vary between 1 µm to 400 µm, preferably between 10 µm to 200 µm.

The increasing of the depth and/or width of the imperfections in particular allows to ensure an essentially uniform and/or equal emission profile of the laser light.

The depth and/or width of the imperfections increases in the direction of the distal end of the core for the reason that a higher amount and/or percentage of the intensity of the laser light has, in particular, to be emitted via the imperfections by refraction on the boundary surface. For example, it is sufficient that 1 to 10% of the percentage of the intensity of the laser light is emitted at the "first" imperfection. That can lead to the fact that the intensity of the laser light decreases after the laser light has passed the "first" imperfection. If the same amount of the laser light is intended to be emitted at the "second" imperfection, the intended percentage of the intensity of the laser light to be sent out has to be higher. This can be reached by increasing the width and/or depth of the imperfection.

The resulting power density along the region provided with the imperfections can be controlled by altering and/or customizing the size, placement and/or number of the imperfections, in particular of the grooves. Adjusting the overall dimension and geometry of the imperfections will, in particular, directly impact the amount of light energy leakage and/or radial light energy dissipation, power density delivered along the region provided with the imperfections, direction of light energy, and/or power energy that will escape from the distal end of the core.

In a further preferred embodiment of the present invention, the material of the core contains fused silica, in particular quartz glass. Further, the core can contain optical fibers which can comprise and/or consist of quartz glass. Alternatively or additionally, the material of the cladding, which surrounds the core, can contain fused silica, in particular quartz glass.

Moreover, the material of the core, in particular the fused silica material of the core, can differ from the fused silica material of the cladding, preferably to ensure the different refractive indices.

The fused silica material of the cladding and/or of the core can be doped, in particular to ensure the different refractive indices. In particular, the cladding can be doped with fluorine and/or boron. The core can, alternatively or additionally, be doped with germanium and/or phosphor. Preferably, the cladding is doped with fluorine, wherein the core is not doped. The doping can enable that the cladding has a smaller refractive index than the core so that the light propagation behavior on the border surface to the core is characterized in that the light is transmitted (back) in the core. Thus, the material of the core and the material of the cladding can be dielectric materials, so that the core (with the optical fibers) and the cladding can be dielectric wave guides (non-conducting wave guides).

The preferred material, namely fused silica, of the cladding and the core can exhibit fairly good optical transmission over a wide range of wave lengths. Furthermore, silica is also relatively chemically inert. In particular, it is non-hygroscopic (it does not absorb water). As already mentioned, silica glass can be doped with various materials, wherein one purpose of doping, in particular of the core, is to rise the refractive index (e.g. with germanium dioxide ($GeO_2$) and/or aluminum oxide ($Al_2O_3$)) and another purpose of doping, in particular of the cladding, is to lower it (e.g. with fluorine and/or boron trioxide ($B_2O_3$)).

The material of the cap can comprise glass and/or fused silica. This material of the cap can ensure the fluid tight and/or liquid tight connection between the cladding, which in particular comprises as material fused silica, and the cap. Therefore, glass and/or fused silica—as materials of the cladding and cap—can be welded and/or fused in the fused regions.

The length of the region provided with the imperfections, preferably the grooves, can range between 0.1 to 30 mm, preferably between 1 to 15 mm, more preferably between 3 to 4 mm. The length of the region provided with the imperfections, preferably the grooves, corresponds in particular to the length over which the light is emitted and/or sent out. Therefore, the efficiency of the use of the device is increased for the reason that the laser emission profile is in particular not related to a so-called "front firing". Furthermore, the emission of the laser light can be circumferential around the core, preferably around 360 degrees.

Furthermore, the distal end of the core can be terminated by a reflector. The reflector can be formed by the distal end of the core and/or the cladding. The core and/or the cladding can end and/or lead into the reflector.

The reflector can have a conical shape, wherein the cone angle of the reflector designed as a reflecting cone can further be around 60 degrees.

The shape of the reflector can have an influence on the refractive behavior of the laser light. The laser light can either be refracted or reflected on the boundary surface of the reflector. The geometry of the reflecting cone (reflector) can therefore be designed in such a way that the laser light is emitted and/or sent out via the reflecting cone and/or in such a way that at least 20%, preferably at least 50%, of the intensity of the laser light that hits the reflector is reflected, in particular by total internal reflection. The greater the cone angle is, the higher the percentage of the reflected laser light can be. Additionally or alternatively, the reflector can have a conical reflecting cone surface, wherein the cone angle of the reflecting cone is about 68 degrees to 90 degrees.

The term "reflector" should, thus, be understood in particular in a broad sense so that the reflector can also be designed to at least partially refract light.

Preferably, the proximal end of the bore of the cap is provided with a section, preferably in a non-fused region, having an increased inner diameter corresponding to the outer diameter of the buffer layer and/or the outer diameter of the core. The buffer layer can be part of the protective sheath, wherein the buffer layer can surround the cladding and/or the core in the section having the increased inner diameter corresponding to the outer diameter of the buffer layer.

Furthermore, the section having the increased inner diameter at the proximal end of the cap is glued to at least one buffer layer and/or to the core and/or to the cladding. The buffer layer can be placed at the proximal end of the cap and can further be placed adjacent to the cap. The glue can further be additionally provided, in particular to ensure a smooth transition between the outer surface, in particular the outer diameter, of the cap and that of the outer sheath. The glue can connect the cap to the outer sheath. Further, the glue can connect the buffer layer to the inner surface of the cap.

In particular, the outer surface of the cap is glued to the outer sheath, wherein the inner surface of the cap can be at least partially glued to the buffer layer, the core and/or the cladding and/or the outer sheath.

The outer surface, in particular the outer diameter, of the cap and/or the outer surface, in particular the outer diameter, of the protective sheath and/or the outer surface, in particular the outer diameter, of the outer sheath may represent the smaller outer surface, in particular the smaller outer diameter. In particular, the outer diameter of the cap may be larger or smaller than the outer diameter of the protective sheath and/or outer sheath.

Moreover, the glue can be placed between the outer sheath and the cap and/or in the section to connect the cap to the cladding and/or to the core, preferably in a non-fused region.

In particular, the inner surface of the bore of the cap is provided with an anti-reflective coating. Therefore, the propagation behavior of the laser light can be influenced in the bore of the cap, in particular in such a way that the laser light is transmitted to the region provided with the imperfections.

In particular, the imperfections, preferably the grooves, are produced by cutting by means of a $CO_2$ laser beam by rotating the core and its optical cladding around its longitudinal axis relative to the laser beam and axially moving the laser beam and/or the core and its cladding around the longitudinal axis of the core in a synchronized manner with the rotation of the core. This production of the imperfections is easy in handling and can create well defined imperfections to manipulate the propagation behavior of the laser light in an efficient way.

In order to maximize the light output density, this spatial distance of imperfections/grooves in longitudinal direction must be minimized. This, however, would in particular lead to fairly rapid change in depth of the imperfections/grooves and fairly steep flange angles and an imperfection/groove surface which is oriented almost perpendicular to the direction of light propagation in the optical fiber. The latter would in particular give rise to undesired back-scattering of the laser light into the optical fiber and eventually back into the source.

An optimization of light output density can be obtained in particular by providing second or more additional spiral grooves along the longitudinal axis of the optical fiber, in particular resulting in the desired more uniform and dense radiation along the longitudinal axis of the core, said grooves extending through said optical cladding into said core, successive grooves of the respective spiral grooves are alternating along the longitudinally extending outer surface of the core and its optical cladding.

Preferably, the additional second or more spiral grooves alternate along the longitudinal axis of the core with the first spiral grooves on the outer surface of the core and its optical cladding, resulting in a more uniform and dense distribution of the light emitted by the grooves, so that in spite of the flank angle of individual grooves required for refracting the light propagating within the fiber optic core in generally radial directions, the laser light output may be concentrated on a shorter length of the bared distal end of the fiber core and its optical cladding.

With embodiments wherein two or more spiral grooves are provided, the starting points of the spiral grooves are preferably angularly offset in the circumferential direction of the core by 360 degrees divided by the number of grooves in the circumferential direction of the core.

This enables a uniform emission profile of the laser light which is emitted at the boundary surfaces of the grooves.

In another preferred embodiment two or more spiral grooves can have substantially the same pitch angle value relative to the longitudinal axis of the core and can further extend in the same direction. This geometry of the spiral grooves can enable a uniform emission profile of the laser light and is additionally easy to produce according to the symmetric and/or regular geometry of the grooves.

Alternatively or additionally, two or more spiral grooves can have the substantially same pitch angle value, wherein they extend in opposite directions, such that successive grooves of the respective pairs of the spiral grooves cross each other.

The double helical and/or spiral configuration of the grooves may ensure a uniform and/or a complete—in particular even around 360 degree—treatment of the vein and/or vessel. A double helix groove configuration consists of two congruent helices in particular with the same axis that differ by translation along the axis.

Furthermore, the pitch angle value of the spiral grooves, relative to the longitudinal axis of the core, is selected, in particular, to be about 60 degrees. In experiments that have been carried out with regard to the present invention it has been found that the pitch angle of the spiral grooves of about 60 degrees enables a uniform emission profile which is in particular required and/or advantageous for the use in medical application "phlebology".

The depth of the imperfections/grooves increases preferably in the direction to the distal end of the core to obtain a more uniform light distribution.

In addition, the invention relates to a method for production of a device for treatment of body tissue according to one of the above mentioned embodiments.

In the inventive method the outer surface of the optical cladding is fused in the region—at least partially—between the imperfections to the inner surface of the cap, in particular the inner diameter of the cap. Alternatively or additionally, the outer surface of the optical cladding extending over a distance in front and/or behind the region provided with the imperfections is fused to the inner surface, in particular the inner diameter, of the cap.

It is to be understood that reference is made to the previous remarks regarding the inventive device which also apply in the same way to the inventive process and/or method. To avoid unnecessary explanations, reference is made to the aforementioned comments on the preferred embodiments of the inventive device.

The inventive fusing can ensure the material-locking connection between the cladding and the cap. Accordingly, the safety for the patient during the medical treatment with the device is increased. The cap cannot be pulled off the cladding and/or the core during the treatment of the body tissue, in particular when the device is in the vessel and/or in the vein.

A vacuum according to the invention is in particular to be understood as a partial vacuum that can be reached in a laboratory, wherein in the partial vacuum there is negative pressure. In particular, as a "vacuum" a low vacuum up to an ultra-high vacuum is to be understood according to the invention.

Preferably, the light diffuser, more preferably the cap and/or the cladding, is heated at least in the regions to be fused, in particular so that the cap at least partially collapses and is fused to the optical cladding and/or the core. A vacuum can be applied to the still open end of the cap before and/or during the heating, in particular so that the cap can collapse to the cladding and/or core in a vacuum environment.

The material of the cap, in particular glass and/or fused silica, can be fused due to the heating of the cap and/or the cladding to the cladding and/or the core. The materials of the cap and the cladding and/or the core are firmly bonded after the cap has collapsed in the fused regions. Those regions can extend circumferentially and/or in a 360 degrees manner around the core and/or are provided partially, namely in the fused regions (partial areas). The design of the fused regions can in particular vary according to the regions that have been heated. The region in which the cap and/or cladding is heated is in particular the region in which the cap collapses on the cladding and can therefore be the so-called "fused region" in which the cap is in particular inseparably connected to the cladding and/or the core.

In a further preferred embodiment of the present invention, a part of the protective sheath from the distal end of the wave guide is removed, preferably the part being longer than the length of the section of the core and its cladding to be provided with the imperfections, in particular the grooves.

Alternatively or additionally, the outer sheath of the protective sheath is removed, in particular the length substantially corresponding to the length of the increased diameter portion at the proximal end of the cap. The removal of the protective sheath and/or the outer sheath of the protective sheath can in particular be carried out before the cap is fused to the cladding. It is also possible that the sheath and/or the outer sheath is removed after the cap is fused to the cladding and/or the core. The removal of the protective sheath enables the arrangement of the cap over the cladding. The protective sheath can be provided to protect the core during the use and/or the transport.

Moreover, according to the method of the present invention, the reflector at the distal end of the bared core and its cladding can be provided, in particular by removing the material of the core and/or the cladding. The removing of the material of the core and/or cladding can be carried out before the cap is fused to the cladding.

The removal of the material of the core and/or the cladding can be carried out in such a way that the reflector is designed as a reflecting cone. The cone angle of the reflecting cone can vary between 60 to 90 degrees. The geometry of the reflecting cone of the reflector can further influence the refraction and/or reflection behavior of the light that hits the reflector. Either a reflection, in particular a total internal reflection, or a refraction of the laser light is to be caused. It may be the case, that both a reflection and a refraction occurs with regard to the attack angle and/or the angle of incidence of the laser light.

In addition, the imperfections, preferably the grooves, can be formed by cutting them through the optical cladding, in particular into the core, by means of a $CO_2$ laser beam and/or a plasma beam.

The size and/or pattern of the imperfections can vary along the length of the core. It may be the case, that a first type of the imperfections only extend into the cladding, wherein another type of imperfections extend into the cladding as well as into the core. Both types of imperfections can be achieved by cutting them with the $CO_2$ laser beam.

The core and its optical cladding can be rotated around its longitudinal axis relative to the laser beam, preferably thereby cutting the imperfections. Further, the laser beam and/or the wave guide and the core and the optical cladding thereof are axially moved along the longitudinal axis of the core in a synchronized manner with the rotation of the core. In this way the spiral grooves of the imperfections can be provided.

After providing the imperfections in the cladding and/or in the core, the cap can be slid over the region provided with the imperfections of the core and over the optical cladding. Preferably, the cap is also slid onto a short length of the buffer layer from which the outer layer/outer sheath of the protective sheath was removed. Therefore, the buffer layer can surround the core and/or the cladding before the cap is provided. Alternatively, a buffer layer can be provided after the cap has been slid over the cladding and/or the core. In another embodiment, there is no buffer layer, wherein the cap is connectable to the outer layer/outer sheath of the protective sheath after the cap is fused to the cladding.

In particular, the proximal end of the cap can be glued to the protective sheath, preferably the buffer layer and/or the outer sheath, after the cap is fused to the core and/or the cladding.

Preferably, the cap can be glued by inserting the device and/or the diffuser comprising the cap with the distal end of the wave guide contained therein through an annular seal at the top of a vacuum tight container having a glue filled flask at the bottom thereof and by applying at least a partial vacuum within the container and/or by introducing the device and/or the diffuser up to beyond the distal end of the cap into the glue filled flask.

The vacuum can be released from the container so that the glue from the flask is sucked into, preferably any, gap(s) between the cap, the buffer layer and the unfused proximal end of the core and its cladding. Alternatively or additionally, the glue is shaped and, preferably, bridges the proximal end of the cap and the outer layer/outer sheath of the protective sheath and, more preferably, any glue still adhering to the outer surface of the cap is removed.

Therefore, the cap can be glued to the outer sheath of the protective layer after the cap is fused to the cladding and/or the core. The gluing of the cap to the buffer layer and/or the outer sheath can be reached by inserting the wave guide and the cap in a glue filled flask.

The gluing of the cap to the outer sheath is a further possibility for connecting the cap to the core. In addition, the glue between the outer sheath and the cap ensures that no liquid, in particular no blood, can reach the boundary between the core and the cladding and/or the cap. In particular, the cap is connected to the outer sheath in a liquid tight and/or fluid tight manner so that no liquid can reach the inner surface of the cap.

Further, a smooth transition of the cap to the outer sheath is provided so that injuries of the body tissue during or after the treatment of the body tissue can be avoided for the reason that there are no sharp edges and/or sharp corners at the proximal end of the cap.

Preferably, the invention relates to a device for treatment of body tissue by means of a light diffuser circumferentially and endoluminally irradiating said tissue by laser light energy, said diffuser being connected at its proximal end to a source of laser light energy via a flexible wave guide comprising a fiber optic core covered by an optical cladding having a refractive index smaller than that of the core, and a protective sheath, the distal end of the wave guide having its protective sheath at least partially removed to bare the core and its optical cladding and being provided with grooves adapted to refract and/or reflect the light propagating within the core and its optical cladding in generally radial directions, a cap transparent to the laser light enclosing the distal end of the core and its optical cladding in a fluid tight and/or liquid tight manner, characterized in that said grooves comprise at least two spiral grooves, said grooves extending through said optical cladding into said core, successive grooves of the respective spiral grooves are alternating along the longitudinally extending outer surface of the core and its optical cladding.

In particular, the device is characterized in that the starting points of said spiral grooves being angularly offset in the circumferential direction of the core by 360 degrees divided by the number of grooves.

More preferably, the device is characterized in that the two or more spiral grooves have substantially the same pitch angle value relative to the longitudinal axis of the core and extend in the same direction.

Moreover, the device can be characterized in that the two or more spiral grooves have substantially the same pitch angle value, but extend in opposite directions, such that successive grooves of respective pairs of the spiral grooves cross each other.

Furthermore, the device is characterized in particular in that the pitch angle value of the spiral grooves relative to the longitudinal axis of the core is selected to be about 60°.

Alternatively or additionally, the device can be characterized in that the depth of the grooves increases in a direction to the distal end of the core.

The device is, preferably, characterized in that the outer surface of said optical cladding is fused in the region between said grooves to the inner diameter to the cap.

Preferably, the device is characterized in that the outer surface of said optical cladding extending over a distance in front and behind the grooved region is fused to the inner diameter to the cap.

More preferably, the device is characterized in that the distal end of the core is terminated by a reflector.

In particular, the device is characterized in that the reflector has a conical shape, the cone angle of the reflecting cone being about 60 degrees.

Furthermore, the device can be characterized in that the reflector has a conical reflecting cone surface, the cone angle of the reflecting cone being about 68 degrees to 90 degrees.

Alternatively or additionally, the device is, preferably, characterized in that the protective sheath comprises at least one buffer layer adjacent to the optical cladding of the core, and an outer sheath.

The device is in particular characterized in that the proximal end of the bore of the cap is provided with a section having an increased inner diameter corresponding to the outer diameter of the buffer layer.

Preferably, the section having the increased inner diameter at the proximal end of the cap is glued to the at least one buffer layer, the glue additionally providing a smooth transition between the outer diameter of the cap and that of the outer sheath.

The inner surface of the bore of the cap is, preferably, provided with an anti-reflective coating.

In particular, the grooves are produced by cutting by means of a $CO_2$ laser beam by rotating the core and its optical cladding around its longitudinal axis relative to the laser beam and axially moving the laser beam and/or the core and its cladding along the longitudinal axis of the core in a synchronized manner with the rotation of the core.

Furthermore, it is clear that in the aforementioned intervals and ranges all interim intervals and individual values are comprised and must be considered as essential for the invention, even if these interim intervals and individual values are not specifically provided.

Further features, advantages, and application possibilities of the present invention are provided in the following description of exemplary embodiments shown in the drawing and the drawing itself. All described and/or illustrated features form, by themselves or in any combination, the object of the present invention, regardless of their summary in the claims and their dependencies.

Preferred embodiments of the device according to the present invention are shown in the enclosed drawing, wherein.

In the figures, which are only schematic and sometimes not to scale, the same reference signs are used for the same or similar parts and components, corresponding or separable properties and advantages being achieved even if these are not repeatedly described.

Figure 1:
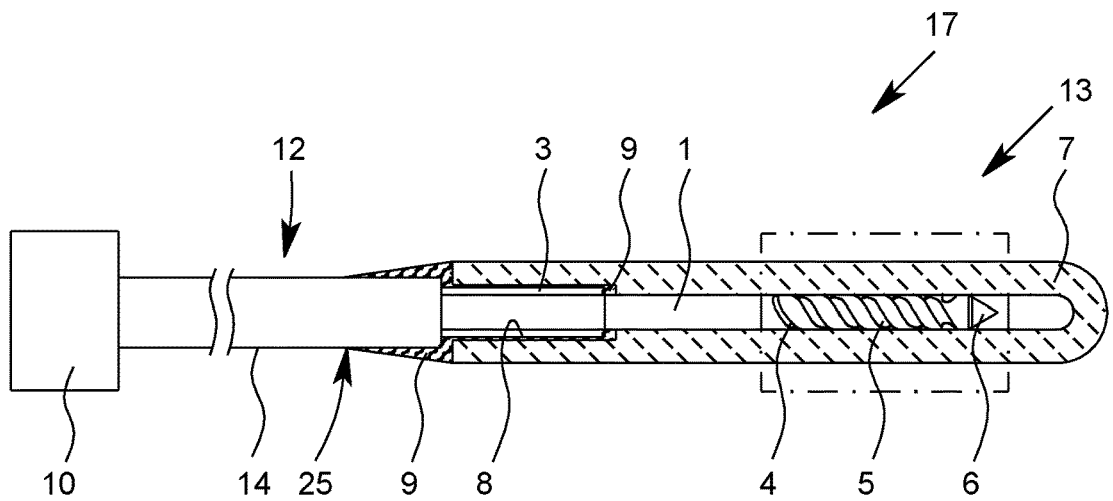
FIG. 1 shows a first embodiment of the diffuser device of the present invention in a schematic cross-sectional side view.

In FIG. 1 a first embodiment of an elongated diffuser device 13 is shown which is connected at its proximal end via a wave guide 12 to a source 10 of laser light. The wave guide 12 is interrupted by broken lines to indicate that it may have any length desired for a specific application.

Figure 2:
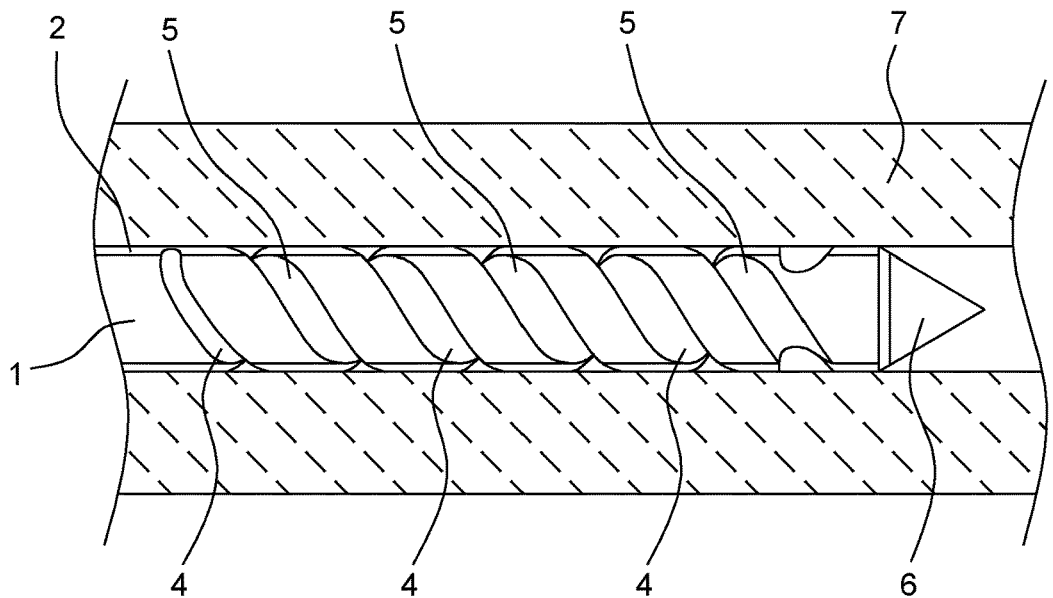
FIG. 2 shows a detail marked in FIG. 1.

The wave guide 12 comprises in a conventional manner an optical fiber core 1 and an optical cladding 2 visible in FIG. 2, which has a refractive index smaller than that of the core 1 so that light radiated by the source 10 into the core 1 may be transferred via the wave guide 12 with a minimum of losses to the diffuser device 13. The optical cladding 2 of the core 1 is covered by an inner or buffer layer 3 (for example "hard clad") and at least one outer layer 14 of a protective sheath 25.

The diffuser device 13 has an active zone marked with dash-dotted lines in FIG. 1 and shown in more detail in FIG. 2. In this zone, the buffer layer 3 and any of the outer layers/outer sheath 14 of the protective sheath 25 are removed, leaving only the optical fiber core 1 and its optical cladding 2. This active zone is adapted to redirect the light propagating along the longitudinal axis of the wave guide 12 in substantially radial directions.

At least this active zone (see dash-dotted lines) is enclosed in a cap 7 transparent to the laser light and having an inner diameter substantially corresponding to the outer diameter of the core 1 and its cladding 2.

Figure 3:
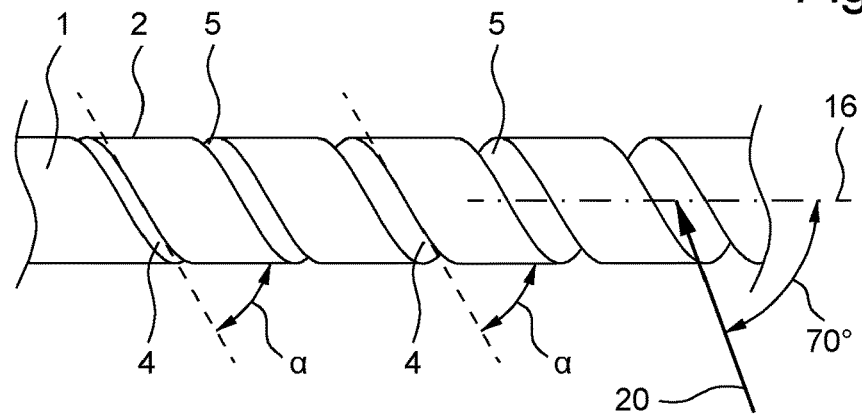
FIG. 3 shows a non-limiting detail of a grooved section of the diffuser device and the method of cutting the grooves.

As may especially be seen from the embodiment shown in FIGS. 1 to 3, within the active zone (see dash-dotted lines), the optical core 1 and its cladding 2 comprise two spiral grooves 4, 5 starting at respective offset starting points around the circumference of the optical core 1 and its cladding 2. These grooves 4, 5 are cut through the cladding 2 and into the outer circumference of the core 1. The number of grooves 4, 5 of course is not limited to two grooves 4, 5, which are only mentioned for explanatory purposes. In general, the starting points of the spiral grooves 4, 5 are preferably angularly offset in the circumferential direction of the core 1 by 360 degrees divided by the number of grooves 4, 5 in the circumferential direction of the core 1.

As may be seen from FIG. 2, the offset starting points of the individual spiral grooves 4, 5 result in the grooves 4, 5 alternating along the length of the outer circumference of the core 1 and its optical cladding 2.

At least some of the circumferential parts of the core 1 and/or the cladding 2 which extend between the grooves 4, 5 and short sections of the core 1 and cladding 2 at both ends of the grooved section along the length of the cap 7 are fused to the inner diameter of the cap 7 thereby resulting in a reliable support for the core 1 and cladding 2 within the active zone (see dash-dotted lines in FIG. 1).

The grooves 4, 5 at the outer surface of the core 1 and its cladding 2 have a predetermined shape depending on the intended direction and concentration of the radial radiation caused by the grooves 4, 5, which result in a re-direction by reflection of the light passing through the core 1 of the wave guide 12 into a radial direction and/or by refraction of this light at the interfaces formed between the grooves 4, 5 and the inner diameter of the cap 7.

The distal end of the core 1 and cladding 2 is terminated by a conical reflector 6 thereby avoiding any axial emissions of the light energy not dissipated by the individual grooves 4, 5 on the first pass through the section of the core 1 provided with the grooves 4, 5. The cone angle of this reflector 6 is about 60 degrees for lateral reflection of this light energy, or may be about 68 to 90 degrees for reflection of this light energy back into the section of the core 1 provided with the grooves 4, 5.

Figure 4:
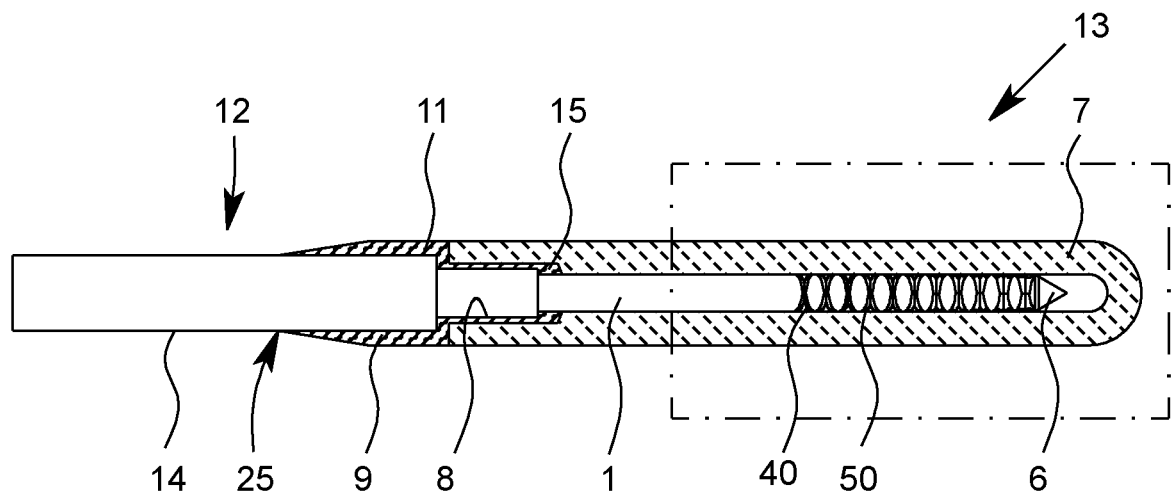
FIG. 4 shows a second embodiment of the diffuser device of the present invention in a schematic cross-sectional side view.

At its proximal end, the inner bore of the cap 7 has an increased inner diameter portion 8 slightly larger than the outer diameter of the buffer layer 3 of the protective sheath 25. Small gaps 11, 15 (as indicated in FIG. 4) are left between the distal end of the increased diameter portion 8 and the distal end of the buffer layer 3 and between the distal end of the outer layer 14 of the protective sheath 25 and the proximal end of the cap 7, respectively. These gaps are filled with glue 9 which also penetrates into the space between the outer circumference of the buffer layer 3 and the inner diameter of the cap 7, and may penetrate over a short distance into the space between the outer diameter of the cladding 2 not fused to the cap 7 and the inner diameter of the cap 7, thereby mechanically securing the cap 7 in a reliable and fluid tight and/or liquid tight manner to the buffer layer 3 of the protective sheath 25 and to the outer layer 14 thereof.

The penetration of the glue 9 into the space between the buffer layer 3 and the increased diameter portion 8 as well as between any portions of the core 1 and its optical cladding 2 not fused to the inner diameter of the cap 7 is favored by the decreased pressure resulting from the cooling of the air or other gaseous medium in the cap 7 after fusing the active zone to the inner diameter, or by other means as set out below.

In this manner and in addition to the fusing of part of the cladding 2 of the active zone (see dash-dotted lines in FIG. 1) to the inner diameter of the cap 7, an increased stability of the device 17 and/or diffuser 13 is obtained.

The glue 9 may also extend over the outer layer 14/outer sheath 14 of the protective sheath 25 as shown in FIG. 1 thereby mitigating any step or any difference between the outer diameters of the cap 7 and of the outer diameter of the outer layer 14/outer sheath 14 of the protective sheath 25.

In FIG. 3, the part of the active region (see dash-dotted lines) in FIG. 1 is shown in more detail. As may be seen from FIG. 3, the flank or pitch angle $\alpha$ of the grooves 4, 5 is preferably about 60 degrees and is produced by rotating preferably the wave guide 12 and the core 1 and the optical cladding 2 thereof and subjecting this active portion (see dash-dotted lines) to a laser beam 20, preferably of a $CO_2$ laser beam, under an angle of about 70 degrees to the longitudinal axis 16 of the core 1 thereby cutting the grooves 4, 5 into the outer surface 19 of the optical cladding 2 and into the core 1 as shown in FIG. 3.

During the rotation of the core 1, the laser beam 20 is moved continuously along the length of the active zone in a synchronized manner with the rotation thereof, either by movement of the laser beam 20 and/or wave of the wave guide 12 and the core 1 and the optical cladding 2 thereof.

Further, the power of the laser beam 20 during its movement from the proximal end to the distal end of the core 1 and/or the duration of exposure of the core 1 and the optical cladding 2 to the laser beam 20 may be increased such that the depth of the grooves 4, 5 increases towards the distal end of the active zone.

The two grooves 4, 5 or any additional grooves are preferably cut in separate steps one after the other.

It is of course also possible to hold the optical core 1 stationary and to rotate a device producing the laser beam 20 or a suitable set of optical mirrors and beam deflection equipment around the core 1. Further, the laser beam 20 may be directed by a suitable set of optical mirrors and beam deflection equipment onto the optical cladding 2 of the core 1.

Instead of using a laser beam 20, also a plasma beam may be used for cutting the grooves 4, 5.

On heating the cap 7 and fusing the optical cladding 2 to the inner diameter of the cap 7, the air or other medium within the cap 7 expands due to the high temperature and leaves the cap 7, and after fusing, the glue 9 is applied and is partially sucked into the gaps mentioned above on cooling down the device and thereby causing a lower pressure within the cap 7. Another method for applying the glue 9 shall be explained below.

Figure 5:
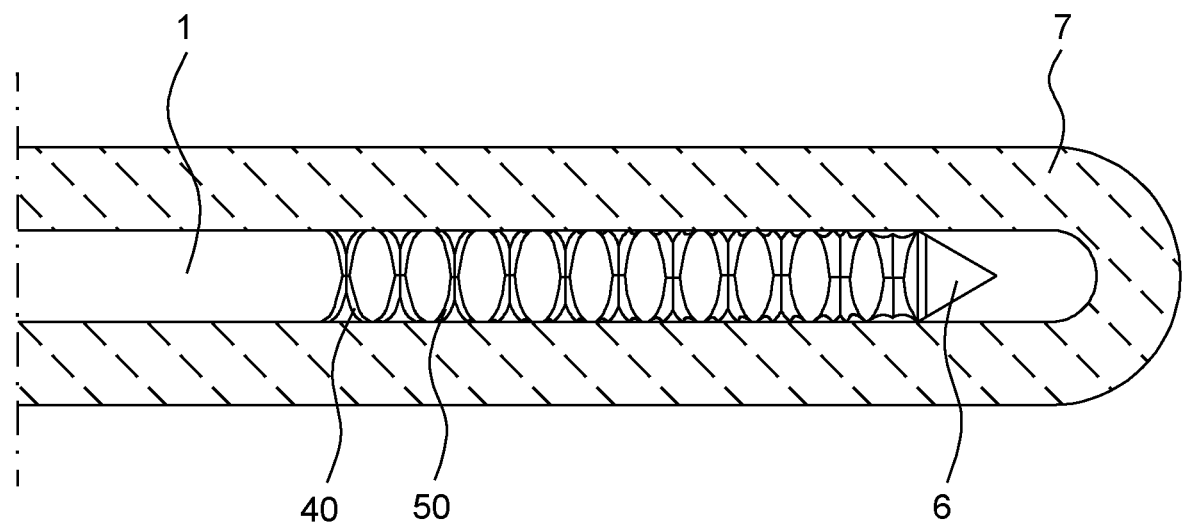
FIG. 5 shows a detail marked in FIG. 4.

The embodiment of the device shown in FIGS. 4 and 5 is similar to the embodiment shown in FIGS. 1 to 3, but differs therefrom by the fact that the two or more spiral grooves 40, 50 have substantially the same pitch angle $\alpha$ value, but extend in opposite directions, such that successive grooves 40, 50 of respective pairs of the spiral grooves 40, 50 cross each other.

In the following, further embodiments of the proposed device 17 are described. The previous explanations apply in particular correspondingly or in addition, even without repeated description.

Figure 6:
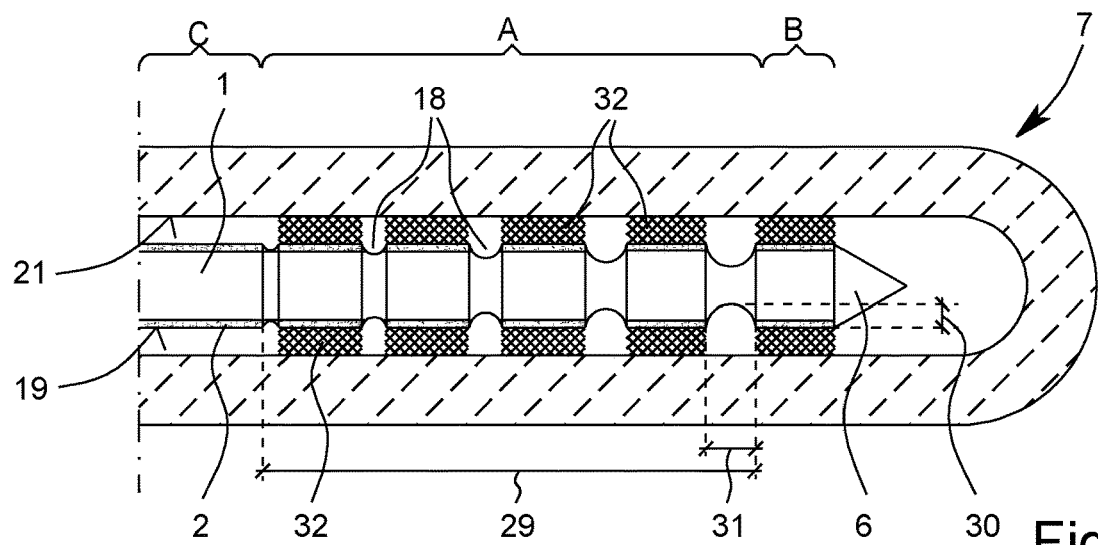
FIG. 6 shows a schematic cross-sectional view of the distal end of the diffuser according to another embodiment of the inventive device.

FIG. 6 shows a distal end of the device 17 and/or the diffuser 13 for treatment of a body tissue. A device 17 and/or a diffuser 13 for the treatment of body tissue is shown in FIG. 1. The device 17 and/or the diffuser 13 can be used for the permanent occlusion of varicose veins, preferably in the lower limbs, and/or for the medical application phlebology and/or for the permanent occlusion of varicocele and/or vascular malformations and/or for the use in aesthetic surgeries, preferably laser assisted lipolysis, and/or for tumor treatment by means of laser induced thermotherapy and/or photodynamic therapy. The device 17 and/or the diffuser 13 can be at least partially inserted in the body tissue, in particular in the vessels and/or the veins.

The device 17 for the treatment of body tissue has a light diffuser 13 which circumferentially and endoluminally irradiates said tissue by laser light energy. The laser light is irradiated in the active region A. Said diffuser 13 is connected at its proximal end to a source 10 of laser light energy by a flexible wave guide 12 comprising a fiber optic core 1 covered by an optical cladding 2 having a refractive index smaller than that of the core 1.

In FIG. 6 the wave guide 12, namely the distal end of the wave guide 12, is shown with its core 1 and its optical cladding 2. The source 10 of the laser light is shown in FIG. 1.

FIG. 6 shows that in the cladding 2 and/or in the core 1 imperfections 18 are provided, which are designed as recesses and are adapted to direct the light, preferably to refract and/or reflect the light propagating within the core 1 and/or its optical cladding 2 in generally radial directions.

The refractive index of the cladding 2 is smaller than that of the core 1 so that the light propagates through the core 1. The imperfections 18 create boundary surfaces on which the laser light is refracted and/or reflected. These boundary surfaces can influence the propagation behavior of the laser light. Further, over and/or by the imperfections 18 the laser light is (partially) sent out and/or coupled out so that a, in particular specified, percentage of the intensity of the laser light can be transmitted and can "hit" the body tissue.

Moreover, FIG. 6 shows that a cap 7 is provided which is transparent to the laser light enclosing the distal end of the core 1 and its optical cladding 2 in a fluid tight and/or liquid tight manner. The cap 7 can surround the cladding 2 and the core 1 at the distal end of the wave guide 12. The cap 7 can be inserted in the body tissue, wherein the laser light is transmitted via the cap 7. The refractive index of the cap 7 is of such a size that with regard to the refractive index of the core 1 and the cladding 2, the laser light can pass the cap 7 to be sent out and/or to be emitted and/or to be coupled out by the diffuser 13. Also, the cap 7 protects the core 1 and the cladding 2 from the liquid, in particular the blood, in the body tissue. Moreover, the cap 7 can increase the stability of the distal end of the diffuser 13 which is inserted in the body tissue.

FIG. 6 shows—in a schematic view—that the outer surface 19 of said optical cladding 2 is fused in the region A between said imperfections 18 to the inner surface, preferably the inner diameter, of the cap 7. The region A between the imperfections 18 is fused to the inner surface 21 of the cap 7 in such a way that the cap 7 is irremovably connected to the cladding 2.

Furthermore, the outer surface 19 of the optical cladding 2 extending over a distance in front and/or behind (with regard to the direction of the light propagation in the core 1) the region A provided with the imperfections 18 can also be fused to the inner surface 21, in particular the inner diameter, of the cap 7.

The cladding 2 is at least fused in one region (fused region 32) to the inner surface 21 of the cap 7. The fused region(s) 32 can be at least a part of the region A between the imperfections 18 and/or of the region C in front and/or of the region B behind the region A provided with the imperfections 18.

FIG. 6 shows that at least a part of the region B behind the region A provided with the imperfections 18 is fused to the inner surface 21 of the cap 7.

Figure 7:
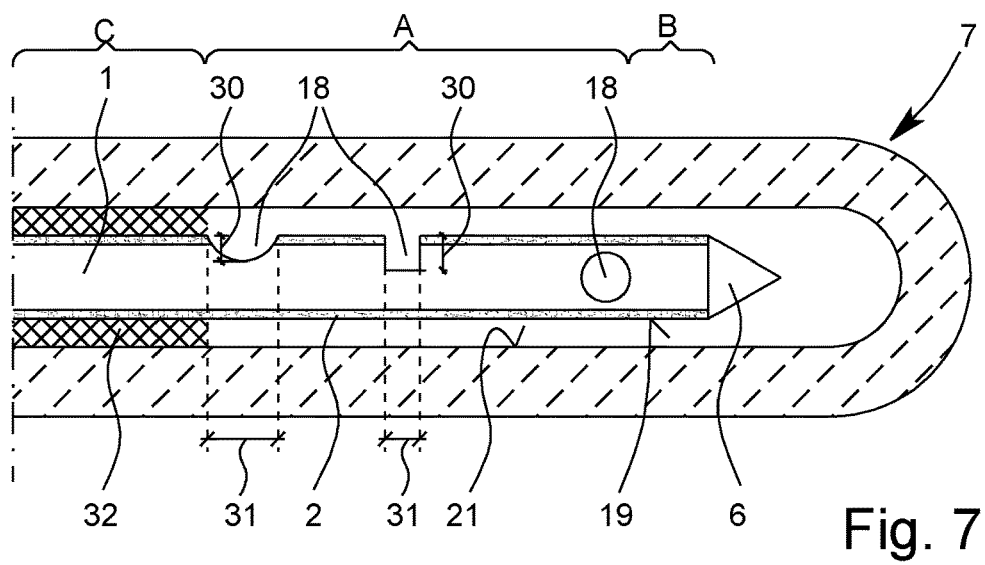
FIG. 7 shows a schematic cross-sectional view of the distal end of the diffuser according to another embodiment of the inventive device.

FIG. 7 shows that the region C in front of the imperfections 18 is fused—at least partly—to the inner surface 21 of the cap 7.

Figure 8:
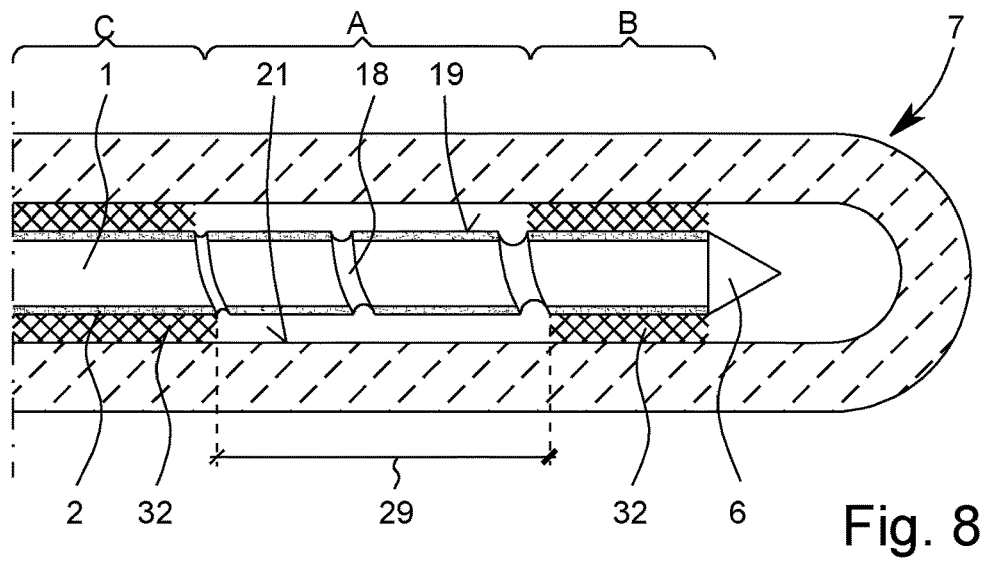
FIG. 8 shows a schematic cross-sectional side view of the distal end of the diffuser of another embodiment of the inventive device.

FIG. 8 shows that the region C in front of the region A provided with the imperfections 18 is at least partly fused to the inner surface 21 of the cap 7, wherein also a fused region 32 is provided in the region B behind the region A provided with the imperfections 18.

It has to be understood that the FIGS. 6, 7, 8 and 12 show the fused region 32 in a schematic view due to the fact that the thickness of the fused region 32 is shown in an enlarged view.

The region B is in the figures referring to a region of the core 1 and/or the cladding 2 behind the region A provided with the imperfections 18, wherein in the region B the reflector 6 is in particular not included.

The region C is in particular indicating a region in front of the region A provided with the imperfections 18. The region C can extend from the "beginning"—with regard to the laser light propagation—of the region A to the proximal end of the cap 7 and/or to the outer sheath 14 or can refer to a part of the region in front of the region A provided with the imperfections 18.

Figure 12:
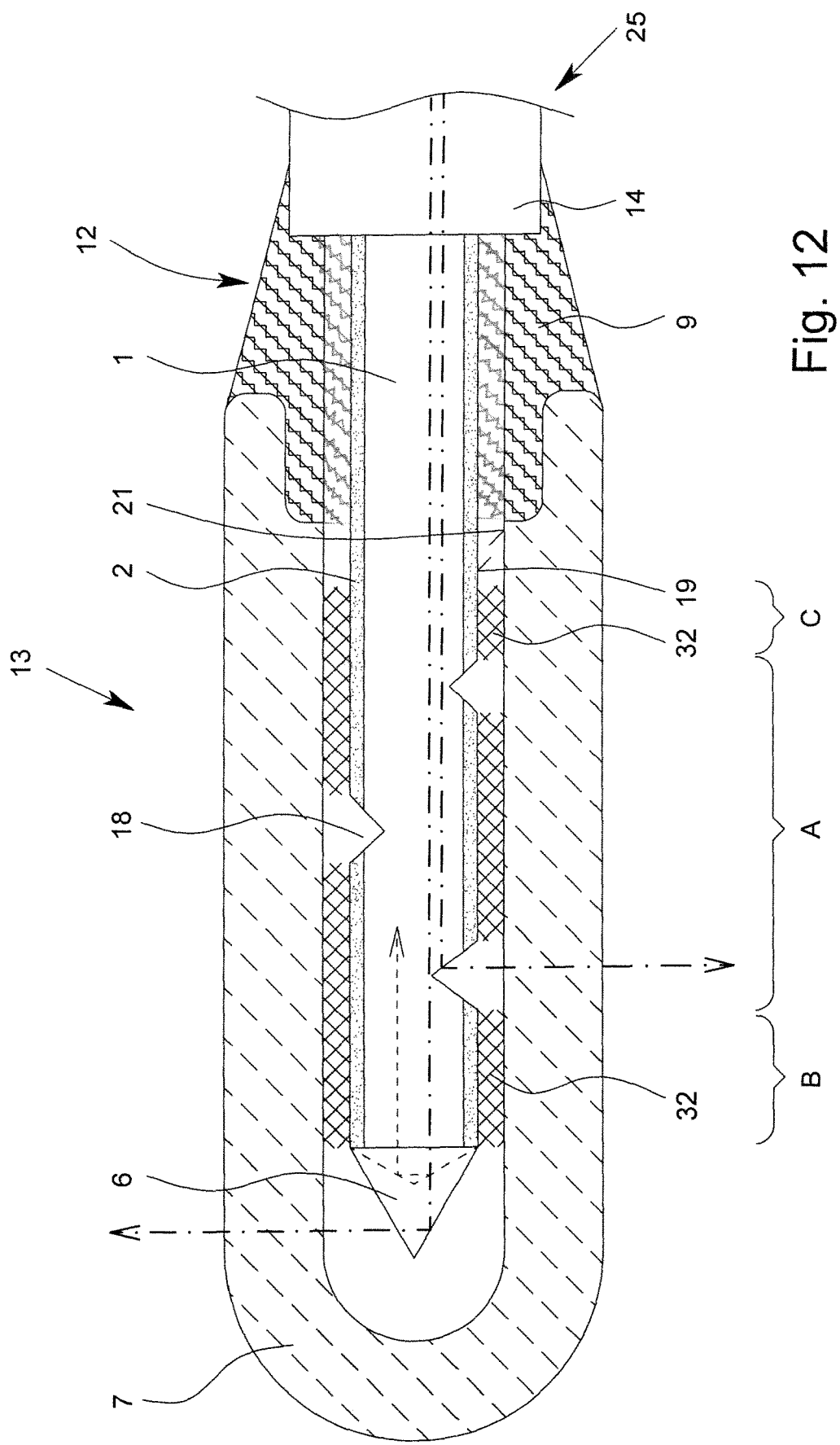
FIG. 12 shows a schematic cross-sectional view of the distal end of the diffuser of the inventive device according to another embodiment.

That the region C refers to a part of the region in front of the region A provided with the imperfections 18 is indicated in FIG. 12. The region C refers at least to a part/area/region in front of the region A provided with the imperfections 18.

The fused region(s) 32 can be in the region A, B and/or C. It has to be understood that the fused region(s) 32 can be at least a part of the region A, B and/or C. In the fused region(s) 32 the outer surface 19 of the cladding 2 is fused to the inner surface 21 of the cap 7, in particular to firmly attach the cap 7 to the cladding 2.

Further, FIG. 12 shows a partial area of the region in front of the region A which is free from a fused region 32 (has a non-fused region), in particular for being filled with glue 9 to be attached to the outer sheath 14.

In particular, the outer surface 19 of the optical cladding 2 is fused continuously and/or circumferentially and/or fully in the region A between the imperfections 18 to the inner surface 21, in particular the inner diameter, of the cap 7 and/or the outer surface 19 of the optical cladding 2 extending over a distance in front and/or behind the region A provided with the imperfections 18 is fused continuously and/or circumferentially and/or fully to the inner surface 21, in particular the inner diameter, of the cap 7 (that means in the region B and/or in the region C). The circumferential fusing of the cap 7 to the cladding 2 can therefore be designed in a 360 degree circumferential manner.

Moreover, it is not shown in the figures that the outer surface 19 of the optical cladding 2 can be fused partially, preferably in a point-like manner and/or with longitudinal welds and/or with a patterned structure, in the region A between said imperfections 18, to the inner surface 21 of the cap 7 and/or in the region B behind the region A provided with the imperfections 18 and/or in the region C in front of the region A provided with the imperfections 18.

Also a combination of a circumferentially and/or fully fusing of the cap 7 to the cladding 2 at least in one part of a region A, B, C and a partly fusing of the cap 7 to the cladding 2 in at least one part of the regions A, B, C is possible.

In particular, the cladding 2 is fused to the cap 7 in such a way that the cladding 2 and the cap 7 are firmly bonded, namely in a material-locking manner. This can be provided at least in one part of the regions A, B, C, namely in the fused region(s) 32.

Figure 13:
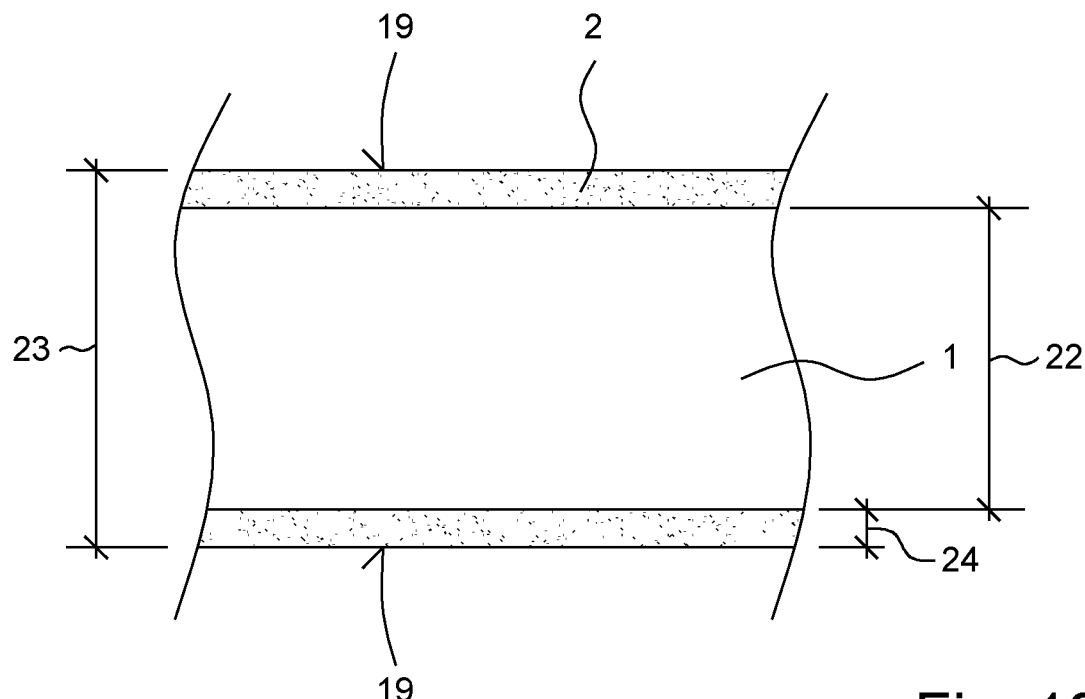
FIG. 13 shows a cross sectional side view of the core and the cladding.

FIG. 13 shows that the core 1 has an outer diameter 22 between 100 and 1000 µm and in particular between 350 and 650 µm. The cladding 2 can have an outer diameter 23 between 110 and 1200 µm and in particular between 400 and 650 µm. In the embodiment according to FIG. 13 the sheath thickness 24 of the cladding 2 is between 1 to 40%, in particular between 5 to 15%, of the outer diameter 22 of the core 1. Preferably, the sheath thickness 24 of the cladding 2 is around 10% of the outer diameter 22 of the core 1.

FIG. 1, FIG. 12 and FIG. 4 show the protective sheath 25. The protective sheath 25 can be at the distal end of the wave guide 12. The protective sheath 25 can comprise at least one buffer layer 3 adjacent to the optical cladding 2 of the core 1 and/or an outer sheath 14, also referred to as jacket. The outer sheath 14 (jacket) can prevent the breaking of the core 1 during the use and transport of the wave guide 12. Furthermore, the protective sheath 25 and/or the outer sheath 14 (jacket) can be designed as a, preferably extruded, plastic coating.

The buffer layer 3 can be additionally provided to the outer sheath 14. In FIG. 1 an embodiment is shown which comprises the buffer layer 3 as a part of the protective sheath 25. In the embodiment according to FIG. 12 there is no need for a buffer layer 3.

The protective sheath 25 and/or the outer sheath 14 can be joined to the cap 7, which is shown in FIGS. 1, 4, and 12.

FIG. 12 shows that the protective sheath 25 and/or its outer sheath 14 is at least partially removed at the distal end of the wave guide 12 to bare the core 1 and its optical cladding 2.

FIG. 6 shows that the imperfections 18 extend into the cladding 2, preferably to bare the core 1. The "first" imperfection 18 (with regard to the direction of the light propagation in the core 1) in the embodiment shown in FIG. 6 extends at least into the cladding 2. Additionally, the imperfections 18 can extend also into the core 1, namely in particular in the outer circumference of the core 1. The form and depth of the imperfections 18 can influence the propagation behavior of the light. The light can be refracted on the boundary surface created by the imperfections 18. The laser light refracted on the boundary surface of the imperfections 18 can be transmitted via the cap 7.

FIG. 12 shows that the laser light (see dash-dotted lines) can be refracted on the boundary surface of the imperfections 18 and therefore be emitted and/or coupled out by the diffuser 13. It is not shown in FIG. 12 that the laser light can also be reflected on the boundary surface of the imperfections 18.

In FIG. 6, one type of the imperfections 18 extend solely into the cladding 2, wherein another type of the imperfections 18 extend into the core 1 as well as into the cladding 2.

FIGS. 1 to 5 show that the imperfections 18 are designed as grooves which are adapted to refract and/or reflect the light propagating within the core 1 and its optical cladding 2 in generally radial directions.

FIG. 3 shows that said grooves 4, 5 comprise at least two spiral grooves 4, 5 which extend through said optical cladding 2 into said core 1. The successive grooves 4, 5 of the respective spiral grooves 4, 5 are alternating along the longitudinally extending outer surface 19 of the core 1 and its optical cladding 2.

The imperfections 18 designed as grooves can also have a different form, in particular a patterned structure.

Figure 9:
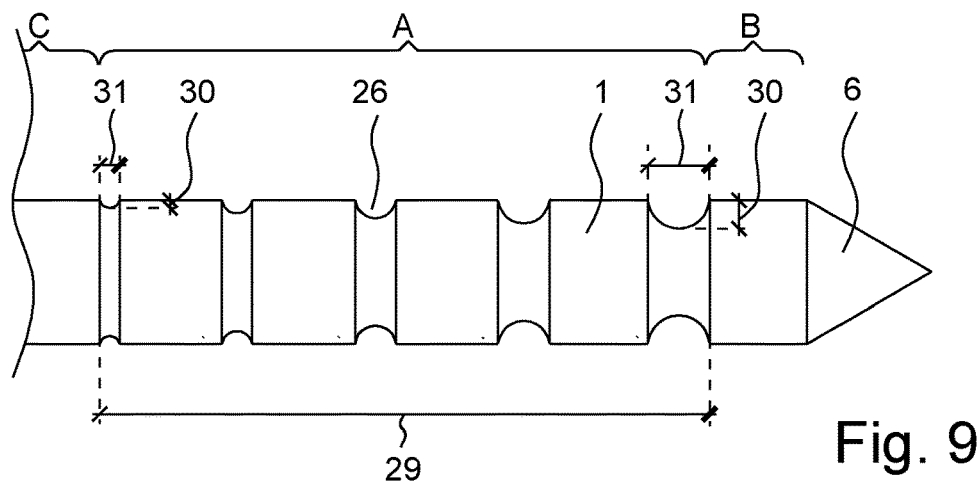
FIG. 9 shows a schematic perspective side view of the core according to another embodiment of the inventive device.

At least one groove can be designed as a circular and/or elliptical groove 26, which is for example shown in FIG. 9. The circular and/or elliptical groove 26 can be circumferential around the core 1. The circular and/or elliptical groove 26 can extend into the cladding 2 and/or into the core 1.

Figure 10:
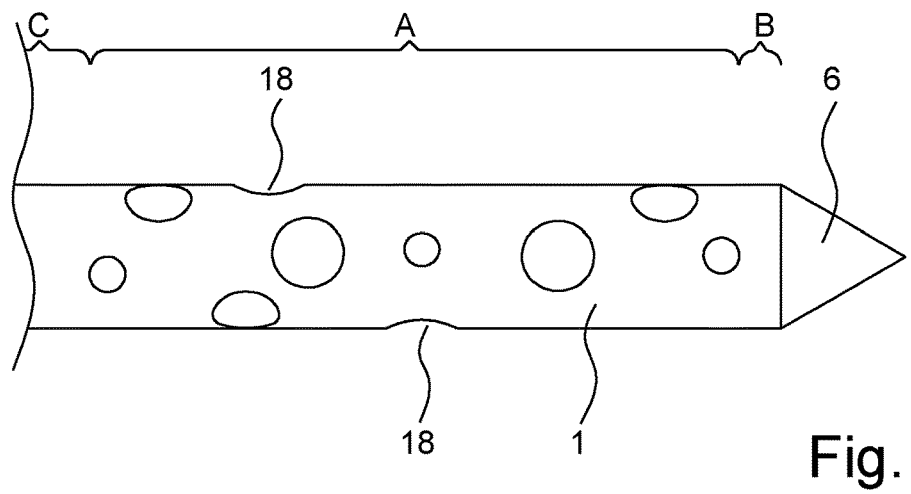
FIG. 10 shows a schematic perspective side view of the core according to another embodiment of the inventive device.

In FIG. 10 it is shown that at least one groove is designed essentially in the form of a spherical cap.

Figure 11:
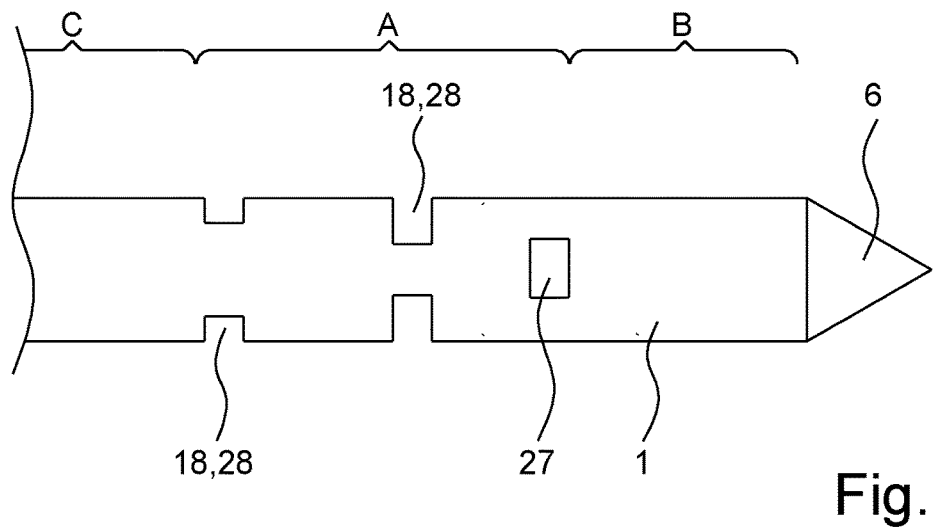
FIG. 11 shows a schematic perspective side view of the core according to another embodiment of the inventive device.

In FIG. 11 it is shown that at least one groove is designed as a longitudinal groove 27. The longitudinal groove 27 can be placed on the outer circumference of the core 1.

In FIG. 11 it is further shown that at least one groove can be designed as a broken groove 28, which includes parts that are not grooved.

It is not shown that at least one groove is a point-like groove, which forms the imperfection 18. The point-like grooves can form a uniform and/or a non-uniform patterned structure.

It is not shown that also different forms of grooves can be combined so that the wave guide 12 can comprise elliptical grooves 26, longitudinal grooves 27 and/or point-like and/or broken grooves 28.

FIG. 6 shows that the depth 30 and the width 31 of the imperfections 18 increases in the direction of the distal end of the core 1. The increasing of the depth 30 and/or the width 31 of the imperfections 18 can be designed in such a way that the percentage of the laser light which is refracted on the imperfections 18 and therefore emitted by the diffuser 13 can be influenced. For example, the depth 30 and/or the width 31 of the imperfections 18 in the direction of the distal end of the core 1 is increased due to the fact that the "first" imperfections 18 need to refract a smaller percentage of the laser light than the imperfections 18 behind. In particular, the depth 30 and/or the width 31 can increase so that a substantially uniform emission profile can be reached, in particular over the length 29 of the region A provided with the imperfections 18.

It is not shown that the length of the imperfections 18 can increase in the direction of the distal end of the core 1.

In particular, the depth 30 and/or the width 31 and/or the length of the imperfections 18 can increase up to 1000%, preferably up to 800%, more preferably up to 400%, in particular with regard to the smallest depth 30 and/or width 31 and/or length of the imperfections 18. Preferably, the greatest depth 30 and/or width 31 and/or length of the imperfections 18 can be around two to four times higher than the smallest depth 30 and/or width 31 and/or length of the imperfections 18.

FIG. 12 shows a core 1 which comprises as material fused silica, in particular quartz glass. The core 1 can comprise optical fibers which can comprise as a material fused silica/quartz glass. The cladding 2 can also contain fused silica as a material, in particular quartz glass. The refractive index of the cladding 2 differs from that of the core 1, wherein the refractive index of the core 1 is greater than that of the cladding 2. This can be achieved in particular by doping either the material of the core 1 and/or the material of the cladding 2. In the embodiment shown in FIG. 12 the fused silica material of the cladding 2 is doped with fluorine.

In another embodiment, which is not shown, the core 1 can be—additionally or alternatively—be doped with germanium.

The fused silica material of the core 1 can differ from the fused silica material of the cladding 2, in particular to achieve the different refractive indices.

Furthermore, in the embodiment which is shown in FIG. 6, the region A provided with the imperfections 18 can have a length 29 between 0.1 to 30 mm and in particular between 3 to 4 mm. The length 29 of the region A provided with the imperfections 18 can influence the emission profile of the laser light. In particular, the laser light is not solely sent or coupled out by the front/outer end (no front firing for the efficient use of laser energy).

FIGS. 9 to 11 show that the distal end of the core 1 is terminated by a reflector 6. The reflector 6 can be formed by the distal end of the core 1 and/or the cladding 2. In particular, the reflector 6 comprises as material the same material as the core 1, wherein further the core 1 can lead into the reflector 6.

Furthermore, FIGS. 9 to 11 show that the reflector 6 has a conical shape, wherein the cone angle is smaller than 90 degrees. In particular, the cone angle can be about 60 degrees or about 68 degrees to 90 degrees. Depending on the form of the reflecting cone the laser light can be refracted and/or reflected on the boundary surface of the reflector 6. A reflection or refraction is also influenced by the angle of incidence of the laser light which hits the boundary surface of the reflector 6. Therefore, the reflector 6 can serve—in the figurative sense—as a mirror and/or in such a way that the laser light can be emitted over the distal end of the cap 7.

Thus, the term "reflector" should be understood preferably in a broader sense, where the reflector 6 can also refract light depending on cone angle, angle of incidence of the light, or the like.

FIG. 12 shows in a schematic view laser light (see dash-dotted lines) that hits the boundary surface of the reflector 6. For the visualization of the reflection and/or refraction of the laser light depending on the cone angle of the reflector 6 two forms of reflectors 6 are shown. The reflector 6 having a greater cone angle can lead to a reflection of the light (dashed line), wherein the laser light is refracted at the boundary surface of the reflector 6 having a smaller cone angle (dash-dotted line).

FIG. 1 shows that the proximal end of the bore of the cap 7 is provided with a section 8 having an increased inner diameter corresponding to the outer diameter of the buffer layer 3. The increased inner diameter of the section 8 can be designed in such a way that the cap 7 can be adjoined to the outer sheath 14, in particular with glue 9.

FIG. 12 shows that the proximal end of the cap 7 is provided with a section having an increased inner diameter corresponding to the outer diameter 22 of the core 1. This section having the increased inner diameter of the cap 7 is filled with glue 9, in particular to further connect the cap 7 to the outer sheath 14 and/or to provide a smooth transition between the outer surface of the cap 7 to that of the outer sheath 14.

Furthermore, in FIG. 1 it is shown that the section 8 having the increased inner diameter of the proximal end of the cap 7 is glued to at least one buffer layer 3. The glue 9 can furthermore be provided to reach a smooth transition between the outer surface, in particular the outer diameter, of the cap 7. Additionally, the smooth transition can also be provided from the cap 7 to the outer sheath 14 of the protective sheath 25.

In FIG. 12 it is shown that the outer sheath 14 can be glued to the cap 7 at the proximal end of the cap 7 with glue 9. The cap 7 also has an increased inner diameter at the proximal end for the connection with the glue 9 and to be adjoined to the protective sheath 25, in particular the outer sheath 14 (also referred to as jacket).

It is not shown that the inner surface 19 of the bore of the cap 7 is provided with an anti-reflective coating, in particular to influence the light propagation behavior, in particular to increase the efficiency of the light emitting profile of the laser light.

In addition, it is shown in FIG. 3 that the imperfections 18, preferably the grooves 4, 5, can be produced by cutting by means of a $CO_2$ laser beam 20 by rotating the core 1 and its optical cladding 2 around its longitudinal axis 16 relative to the laser beam and axially moving the laser beam 20 and/or the core 1 and its cladding 2 along the longitudinal axis 16 of the core 1 in a synchronized manner with the rotation of the core 1.

FIG. 3 shows—in a schematic view—that the laser beam 20 can hit the core 1 in a respective angle. This angle can be around 70 degrees as shown in FIG. 3.

The starting points of the spiral grooves 4, 5 can be angularly offset in the circumferential direction of the core 1 by 360 degrees divided by the number of grooves. It has to be understood that the shown number of grooves is not limited to the number shown in the embodiments according to FIG. 1 to FIG. 14. The number of the imperfections 18 and/or the grooves 4, 5 can depend on the desired laser light emission profile.

FIG. 3 shows that two or spiral grooves 4, 5 can substantially have the same pitch angle α value relative to the longitudinal axis 16 of the core 1 and can extend in the same direction.

Figure 14:
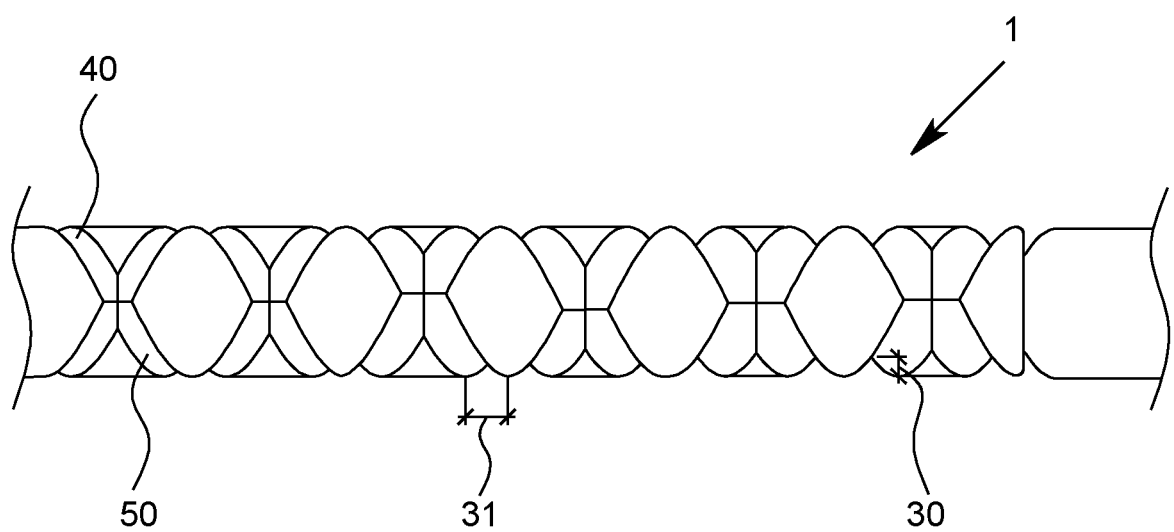
FIG. 14 shows a schematic perspective side view of the core and the cladding according to another embodiment of the inventive device.

In FIGS. 5 and 14 it is shown that the pitch angle α value of the spiral grooves 4, 5 is substantially the same, wherein the spiral grooves 4, 5 can extend in opposite directions such that grooves of respective pairs of the spiral grooves cross each other. The crossing points are in particular shown in FIG. 14 and in FIG. 5.

The pitch angle α value of the spiral grooves 4, 5 can preferably be about 60 degrees relative to the longitudinal axis 16 of the core 1, as shown in FIG. 3.

Figure 15:
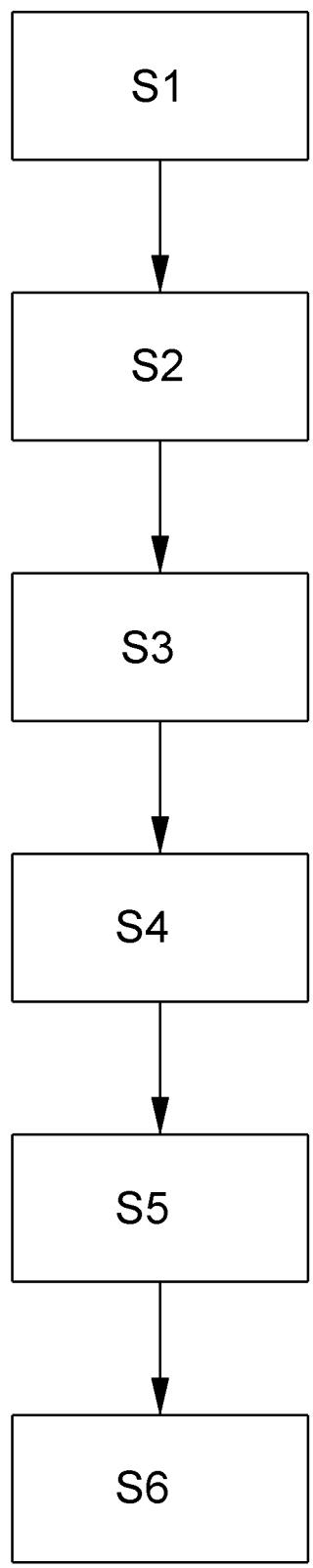
FIG. 15 shows a schematic process scheme of the inventive method.

FIG. 15 shows a process scheme of the method for producing the device 17 and/or the diffuser 13, wherein the signs S1 to S6 refer to single process steps which can be carried out successively. The method is not limited to the steps S1 to S6.

A presently preferred, but not limiting, method for producing a device described above may include the following steps:

Step S1: Removing the protective sheath 25 from a distal end of the wave guide 12 longer than the length of the section of the core 1 and its cladding 2 to be provided with the imperfections 18, in particular the grooves 4, 5, and removing a short length of the outer layer 14 of the protective sheath 25, the short length substantially corresponding to the length of the increased diameter portion at the proximal end of the cap 7.

Step S2: Providing the reflector 6 at the distal end of the bared core 1 and its cladding 2. The reflector 6 can be provided by removing the material of the core 1 and/or the cladding 2, in particular in such a way that the reflector 6 has the geometrical form of a reflecting cone, wherein the cone angle of the reflecting cone can vary between 60 degrees to 90 degrees.

Step S3: Forming the imperfections 18, in particular the grooves 4, 5, by cutting them through the optical cladding 2 into the core 1 by means of a $CO_2$ laser beam 20 or a plasma beam and rotating the core 1 and its optical cladding 2 around its longitudinal axis 16 relative to the laser beam 20 and axially moving the laser beam 20 and/or the wave guide 12 and the core 1 and the optical cladding 2 thereof along the longitudinal axis 16 of the core 1 in a synchronized manner with the rotation of the core 1.

Step S4: Sliding the cap 7 over the section of the core 1 and optical cladding 2 and—optionally—onto a short length of the buffer layer 3 from which the outer layer 14 of the protective sheath 25 was removed.

Step S5: Fusing the cap 7 to the optical cladding 2 so that fused regions 32 occur between the outer surface 19 of the cladding 2 and the inner surface 21 of the cap 7.

The outer surface 19 of the optical cladding 2 can be fused in the region A between the imperfections 18—at least partially—to the inner surface 21 of the cap 7. Alternatively or additionally, the outer surface 19 of the optical cladding 2 extending over a distance in front and/or behind the region A provided with the imperfections 18—in particular the region(s) B and/or C—is fused—at least partially—to the inner surface 21 of the cap 7. In the regions B and/or C the fused region(s) 32 can be designed as at least a part-region/partial area which can be provided circumferentially and/or at least as subparts/subsections (partly fused).

The fusing can be reached by applying a vacuum to the still open end of the cap 7 and heating the device 17 and/or diffuser 13 at the active region A and/or in the region (in particular region A, B and/or C) to be fused (later referred to as fused region 32) such that the cap 7 partially collapses and is fused to the optical cladding 2. Thus, fused region(s) 32 can be achieved, wherein preferably the cap 7 is fused to the cladding 2 and the core 1 between the imperfections 18, in particular the grooves 4, 5, and a short length at the front and end of the active zone "A" (region A).

Step S6 can be carried out after the cap 7 is fused to the core 1 and/or to the cladding 2 (see step S5). In step S6 the following further steps a) to d) can be carried out, preferably successively (one after another):

Step S6: a) Inserting the device 17 and/or diffuser 13 comprising the cap 7 with the distal end of the wave guide 12 contained therein through an annular seal at the top of a vacuum tight container having a glue filled flask at the bottom thereof and applying at least a partial vacuum within the container.

b) Introducing the device 17 and/or diffuser 13 up to beyond the distal end of the cap 7 into the glue filled flask.

c) Releasing the vacuum from the container so that the glue 9 from the flask is sucked into, preferably any, (the) gap(s) between the cap 7, the buffer layer 3 and/or the outer sheath 14 and the unfused proximal end of the core 1 and its cladding 2.

d) Shaping the glue 9 bridging the proximal end of the cap 7 and the outer layer 14 (outer sheath 14) of the protective sheath 25 and removing any glue still adhering to the outer surface of the cap 7.

REFERENCE LIST

1 Core
2 Cladding
3 Buffer layer
4 Groove
5 Groove
6 Reflector
7 Cap
8 Section
9 Glue
10 Source
11 Small gaps
12 Wave guide
13 Diffuser
14 Outer sheath
15 Small gaps
16 Longitudinal axis of 1
17 Device
18 Imperfection
19 Outer surface of 2
20 Laser beam
21 Inner surface of 7
22 Outer diameter of 1
23 Outer diameter of 2
24 Sheath thickness of 2
25 Protective sheath
26 Elliptical groove
27 Longitudinal groove
28 Broken groove
29 Length of A
30 Depth of 18
31 Width of 18
32 Fused region
40 Groove
50 Groove
A Region
B Region
C Region
α Pitch angle

The invention claimed is:

1. A body tissue treatment device comprising:
a light diffuser configured to circumferentially and endoluminally irradiate a body tissue by laser light energy, wherein the diffuser is connected at its proximal end to a source of the laser light energy via a flexible wave guide comprising a fiber optic core covered by an optical cladding having a refractive index smaller than that of the core,
wherein in one or more of the cladding and in the core, imperfections are provided, the imperfections being recesses adapted to direct the laser light energy, to refract and/or reflect the laser light energy propagating within the core and/or the optical cladding in substantially radial directions,
a cap, the cap being transparent to the laser light energy and enclosing a distal end of the core and the optical cladding, the cap being fluid tight,
wherein
the outer surface of the optical cladding is fused, in an irremovably connected manner, in a region between the imperfections to the inner surface of the cap and
the outer surface of the optical cladding extends over a distance in front and/or behind a region provided where the imperfections are fused to the inner surface of the cap.

2. The device of claim 1, wherein one or more of:
the outer surface of the optical cladding is fused continuously in the region between the imperfections to the inner surface of the cap, the outer surface of the optical cladding extending over a distance in front of and/or behind the region provided with the imperfections is fused continuously to the inner surface of the cap, the outer surface of the optical cladding is fused partially in the region between the imperfections to the inner surface of the cap, the outer surface of the optical cladding extending over a distance in front of and/or behind the region provided with the imperfections is fused partially to the inner surface of the cap.

3. The device of claim 1, wherein in the fused regions, in which the cladding is fused to the cap, the cladding and the cap are bonded, in a material-locking manner.

4. The device as claimed in claim 1, wherein the core has an outer diameter between 100 and 1000 μm, and/or
the cladding has an outer diameter between 110 and 1200 μm, and/or
a sheath thickness of the cladding is between 1% to 40%, of the outer diameter of the core.

5. The device as claimed in claim 1, wherein a protective sheath is provided at the distal end of the wave guide, wherein the protective sheath comprises at least one buffer layer adjacent to the optical cladding of the core, and/or an outer sheath, and/or wherein the protective sheath and/or the outer sheath is joined to the cap, and/or wherein the protective sheath and/or the outer sheath is an extruded, plastic coating.

6. The device as claimed in claim 5, wherein the protective sheath and/or its outer sheath is at least partially removed at the distal end of the wave guide to bare the core and its optical cladding, and/or wherein the imperfections extend into the cladding, to bare the core, and/or into the core.

7. The device as claimed in claim 1, wherein the imperfections are grooves adapted to refract and/or reflect the laser light energy propagating within the core and its optical cladding in substantially radial directions,
wherein the grooves comprise at least two spiral grooves, the grooves extending through the optical cladding into the core, wherein successive grooves of the respective spiral grooves are alternating along the longitudinally extending outer surface of the core and its optical cladding,
and/or wherein the grooves comprise at least one circular and/or elliptical groove,
and/or wherein the grooves comprise at least one longitudinal groove,
and/or wherein the grooves comprise at least one point-like and/or broken groove.

8. The device as claimed in claim 7, wherein the depth and/or the width and/or the length of the imperfections, increases in a direction to the distal end of the core,
wherein the depth and/or the width and/or the length of the imperfections increases up to 1000% in relation to the smallest depth and/or width and/or length of the imperfections.

9. The device as claimed in claim 1, wherein the material of the core contains fused silica, and/or the material of the cladding contains fused silica wherein the fused silica material of the core differs from the fused silica material of the cladding,
and/or wherein the fused silica material of the cladding and/or the core is doped, wherein the cladding is doped with fluorine and/or wherein the core is doped with germanium.

10. The device as claimed in claim 1, wherein the region provided with the imperfections has a length between 0.1 to 30 mm.

11. The device as claimed in claim 1, wherein the distal end of the core is terminated by a reflector,
wherein the reflector is formed by the distal end of the core and/or the cladding.

12. The device of claim 11, wherein the reflector has a conical shape, and the cone angle of the reflector is approximately 60 degrees.

13. The device of claim 11, wherein the reflector has a conical reflecting surface, the cone angle of the reflecting surface being between approximately 68 degrees to 90 degrees.

14. The device as claimed in claim 1, wherein the proximal end of the bore of the cap is provided with a section having an increased inner diameter corresponding to the outer diameter of a buffer layer and/or the outer diameter of the core.

15. The device of claim 14, wherein the section having the increased inner diameter at the proximal end of the bore of the cap is glued to one or more of: at least one buffer layer, to the core, and to the cladding, wherein the glue additionally provides a smooth transition between an outer surface of the cap and an outer portion of a protective sheath.

16. The device as claimed in claim 1, wherein the inner surface of the bore of the cap is provided with an anti-reflective coating.

17. The device as claimed in claim 1, wherein the imperfections are produced by cutting with a $CO_2$ laser beam by rotating the core and its optical cladding around its longitudinal axis relative to the laser beam and axially moving the laser beam and/or the core and its cladding along the longitudinal axis of the core in a synchronized manner with the rotation of the core.

18. The device as claimed in claim 1, wherein starting points of spiral grooves corresponding to the imperfections are angularly offset in the circumferential direction of the core by 360 degrees divided by the number of grooves.

19. The device as claimed in claim 1, wherein two or more spiral grooves corresponding to the imperfections have substantially the same pitch angle ($\alpha$) value relative to the longitudinal axis of the core and extend in the same direction.

20. The device as claimed in claim 1, wherein two or more spiral grooves corresponding to the imperfections have substantially the same pitch angle ($\alpha$) value, but extend in opposite directions, such that successive grooves of respective pairs of the two or more spiral grooves cross each other.

21. The device as claimed in claim 20, wherein the pitch angle ($\alpha$) value of the spiral grooves relative to the longitudinal axis of the core is selected to be approximately 60°.

22. A method to produce a device for treatment of body tissue comprising:
providing a light diffuser that circumferentially and endoluminally irradiates the tissue by laser light energy, wherein the diffuser is connected at its proximal end to a source of laser light energy via a flexible wave guide comprising a fiber optic core covered by an optical cladding having a refractive index smaller than that of the core, wherein in one or more of the cladding and in the core, imperfections are provided, the imperfections being recesses adapted to direct the laser light energy, to refract and/or reflect the laser light energy propagating within the core and/or the optical cladding in substantially radial directions, providing a cap, the cap being transparent to the laser light energy and enclosing a distal end of the core and the optical cladding, the cap being one or more of fluid tight and liquid tight, wherein the outer surface of the optical cladding is fused in the region between the imperfections to the inner surface of the cap and the outer surface of the optical cladding extends over a distance in front and/or behind the region provided with the imperfections is fused to the inner surface of the cap, and one or more of:

fusing, in an irremovably connected manner, the outer surface of the optical cladding in the region between the imperfections to the inner diameter of the cap, and fusing, in an irremovably connected manner, the outer surface of the optical cladding extending over a distance in front of and/or behind the region provided with the imperfections to the inner surface of the cap.

23. The method according to claim 22, wherein the device is heated at least in the regions to be fused, so that the cap at least partially collapses and is fused to the optical cladding and/or the core, wherein a vacuum is applied to the still open end of the cap before and/or during the heating.

24. The method according to claim 22, wherein a protective sheath from the distal end of the wave guide is removed, and/or a part of the outer sheath of the protective sheath is removed.

25. The method according to claim 22, wherein a reflector at the distal end of a bared core and its cladding is provided by removing the material of the core and/or the cladding.

26. The method according to claim 22, wherein the imperfections, are formed by cutting the imperfections through the optical cladding by a $CO_2$ laser beam and/or a plasma beam, wherein the core and its optical cladding are rotated around its longitudinal axis relative to the laser beam and/or wherein the laser beam and/or the wave guide and the core and the optical cladding thereof are axially moved along the longitudinal axis of the core in a synchronized manner with the rotation of the core.

27. The method according to claim 24, wherein the cap is slid over the region provided with the imperfections of the core and optical cladding, or the cap is slid onto a short length of a buffer layer from which the outer sheath was removed.

28. The method according to claim 22, wherein after the cap is fused to the core and/or the cladding, the proximal end of the cap is glued to a protective sheath by inserting the diffuser and/or the device comprising the cap with the distal end of the wave guide contained therein through an annular seal at the top of a vacuum tight container having a glue filled flask at the bottom thereof and applying at least a partial vacuum within the container and/or by introducing the diffuser and/or the device up to beyond the distal end of the cap into the glue filled flask, wherein the vacuum is released from the container so that the glue from the flask is sucked into any gap(s) between the cap, the buffer layer and the unfused proximal end of the core and its cladding and/or wherein the glue is shaped and bridges the proximal end of the cap and the outer sheath of the protective sheath.

* * * * *